United States Patent [19]

Horiuchi et al.

[11] Patent Number: 5,389,215

[45] Date of Patent: Feb. 14, 1995

[54] ELECTROCHEMICAL DETECTION METHOD AND APPARATUS THEREFOR

[75] Inventors: Tsutomu Horiuchi; Osamu Niwa; Hisao Tabei, all of Ibaragi; Masao Morita, Tokyo, all of Japan

[73] Assignee: Nippon Telegraph and Telephone Corporation, Tokyo, Japan

[21] Appl. No.: 53,635

[22] Filed: Apr. 27, 1993

[30] Foreign Application Priority Data

Nov. 5, 1992 [JP] Japan .................................. 4-143752

[51] Int. Cl.$^6$ .............................................. G01N 27/26
[52] U.S. Cl. ............................. 204/153.1; 204/153.14; 204/153.2; 204/153.2; 204/412; 204/434
[58] Field of Search ....................... 204/153.1, 434, 412

[56] References Cited

U.S. PATENT DOCUMENTS

| | | | |
|---|---|---|---|
| 4,132,605 | 1/1979 | Tench et al. | 204/434 |
| 4,146,437 | 3/1979 | O'Keefe | 204/434 |
| 4,917,774 | 4/1990 | Fisher | 204/434 |
| 5,298,130 | 3/1994 | Ludwig | 204/434 |
| 5,298,132 | 3/1994 | Reddy et al. | 204/434 |

FOREIGN PATENT DOCUMENTS 2-268265 11/1990 Japan .
3-246460 11/1991 Japan .

OTHER PUBLICATIONS

Osamu Niwa, et al., "Fabrication and characteristics of vertically separated interdigitated array electrodes" J. Electroanal. Chem. 267(1989)291–297.

Tsutomu Horiuchi et al. "Limiting Current Enhancement by Self-Induced Redox Cycling on a Micro-Macro Twin Electrode" Journal of the Electrochemical Society vol. 138, No. 12, Dec. 1991.

Osamu Niwa, et al., "Electrochemical Behavior of Reversible Redox Species at Interdigitated Array Electrodes with Different Geometries: Consideration of Redox Cycling and Collection Efficiency" Analytical Chemistry, vol. 62, No. 5, Mar. 1, 1990.

Akira Fujishima et al., "Denki Kagaku Sokutei Hou" Gihodo Shuppan, pp. 206–208, Nov., 1984.

Primary Examiner—T. Tung
Attorney, Agent, or Firm—Blakely, Sokoloff, Taylor & Zafman

[57] ABSTRACT

In an electrochemical detection method using an apparatus including a first vessel and a second vessel, a reference electrolytic solution in the second vessel, first and second closely spaced working electrodes immersed in a sample solution for measurement in the first vessel, a stripping electrode immersed in the reference electrolytic solution, and an ionic conductor arranged between the first vessel and the second vessel, the reference electrolytic solution contains an electrolyte which can be deposited and dissolved by an electrochemical reaction by applying a potential to the stripping electrode. In a first stage, a pre-electrolysis potential is applied to the first working electrode with the stripping electrode being connected to the second working electrode to deposit the electrolyte in the reference electrolytic solution on the stripping electrode. In a second stage, after the second working electrode is disconnected from the stripping electrode, the potential of the stripping electrode is swept to measure a current generated when the electrolyte deposited on the stripping electrode in the first stage is dissolved from the stripping electrode, and the concentration of an analyte exiting in the sample solution for measurement is determined from the measured stripping current.

13 Claims, 10 Drawing Sheets

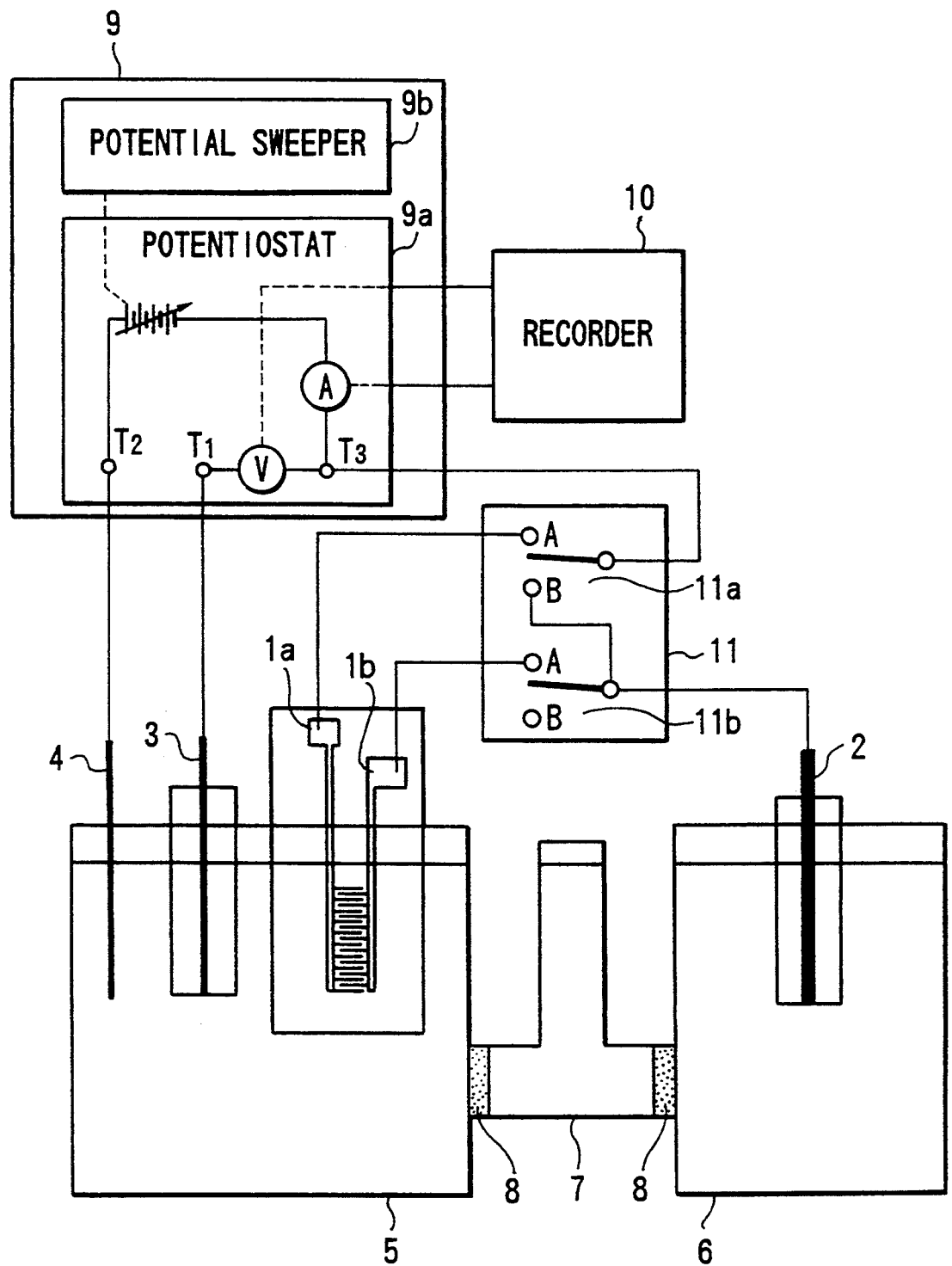
F I G. 1

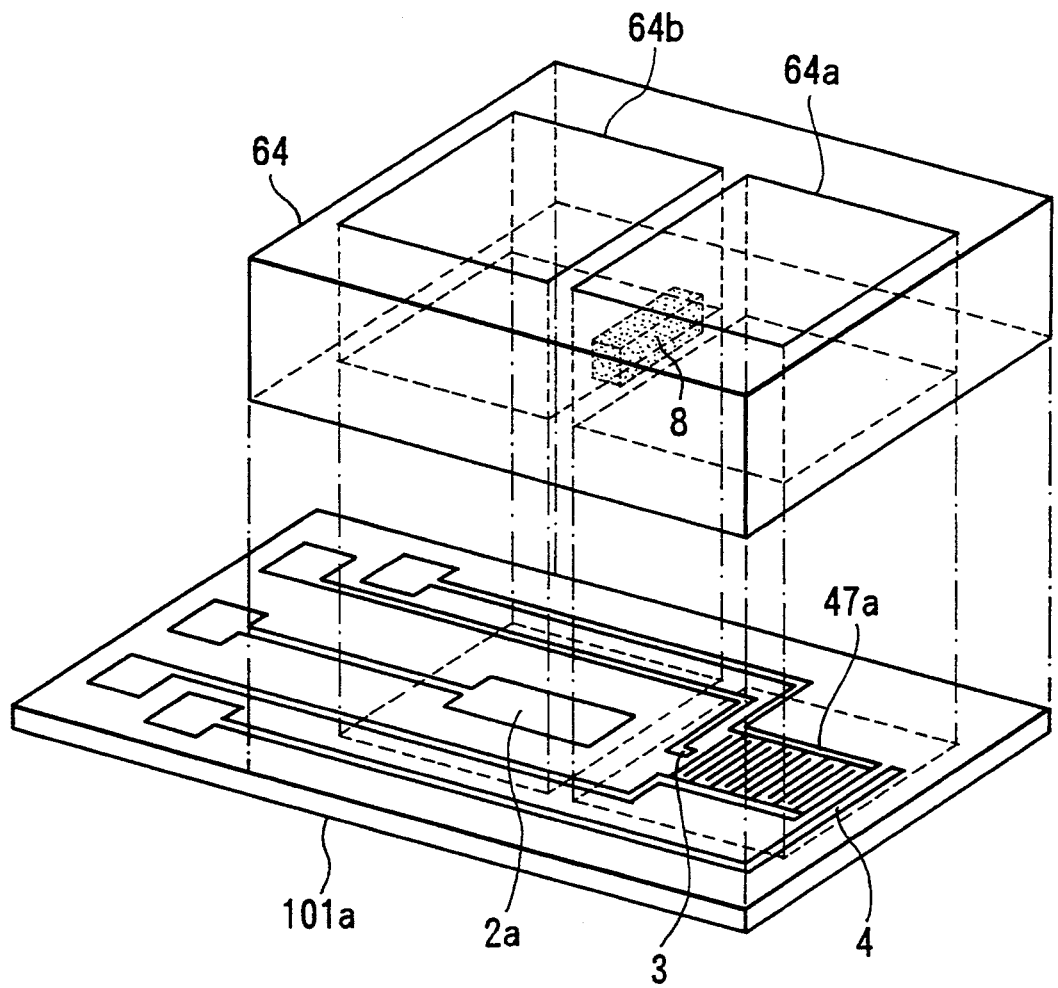
F I G. 6

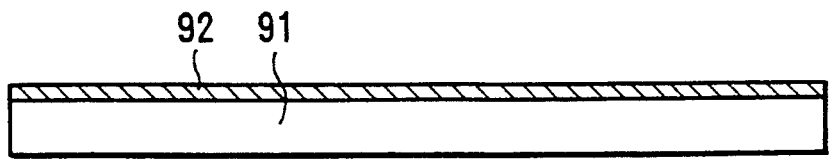
FIG. 9A
FIG. 9B
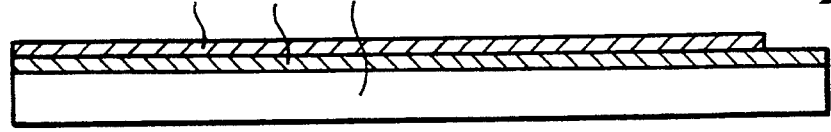
FIG. 9C
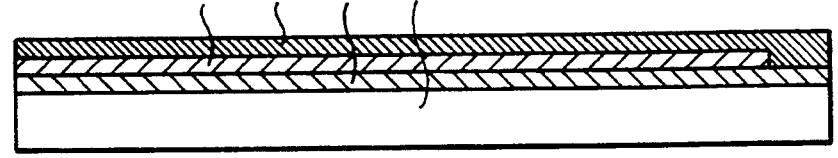
FIG. 9D
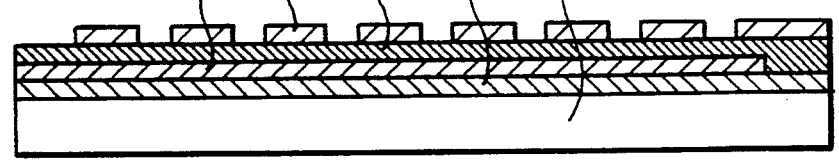
FIG. 9E
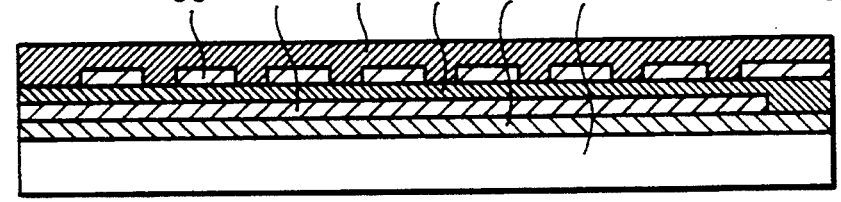
FIG. 9F
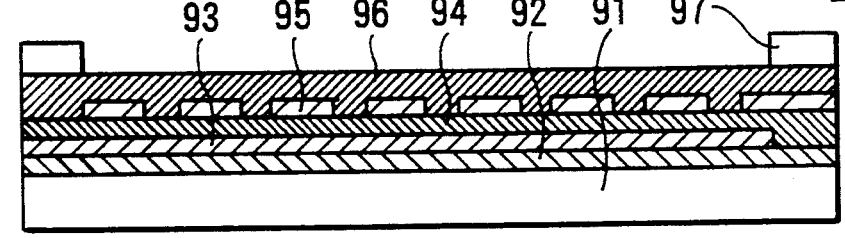
FIG. 9G
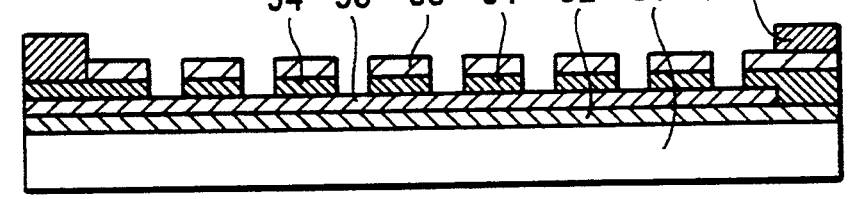

ELECTROCHEMICAL DETECTION METHOD AND APPARATUS THEREFOR

BACKGROUND OF THE INVENTION

The present invention relates to an electrochemical detection method and an apparatus therefor and, more particularly, to an electrochemical detection method and an apparatus therefor, which are used in electrochemical analysis, a chemical sensor, or a biosensor.

An electrochemical detection method is generally used as a method of identifying a material dissolved in the aqueous solution and measuring its amount.

This electrochemical detection method is a method of measuring a current flowing at the electrode in an aqueous sample solution to perform quantitative or qualitative analysis of a material dissolved in the aqueous solution. According to this method, basically, a potential is applied between working and reference electrodes which are immersed in the aqueous sample solution, an oxidation/reduction (redox) reaction of the analyte occurs on the working electrode upon application of the potential, and the magnitude of a current flowing due to this reaction is measured to perform analysis. The electrochemical detection method is commonly used due to its relatively high sensitivity and simpleness.

Typical methods of measuring this current are voltammetry, stripping voltammetry (stripping), and pulse voltammetry methods.

More specifically, the voltammetry method is a method of sweeping the potential of a working electrode immersed in a sample electrolytic solution for measurement with reference to the reference electrode potential, and measuring a current change upon the potential change of the working electrode. When this method is used, the concentration of analyte can be obtained from the measured magnitude of current. In addition, the type of analyte can also be determined from the potential at which the current starts to flow upon potential sweeping. Therefore, both quantitative and qualitative analyses can be simultaneously performed.

However, as this method is performed by sweeping the potential, a charging current flowing in proportion to a potential sweeping rate, electrochemical reactions of coexisting species (e.g., dissolved oxygen and hydrogen ions) except for the current of analyte, and the current caused by the variation of the oxidation states of the electrode surfaces cause noise. As a result, it is difficult to detect an analyte concentration of $\mu mol/l$ or less.

On the other hand, the stripping method is a method of performing analysis in two stages, i.e., pre-electrolysis and stripping. For example, when metal ions dissolved in a sample electrolytic solution is quantitatively analyzed, a predetermined potential enough to reduce metal ions is applied to a working electrode with reference to the reference electrode potential, thereby depositing a metal on the working electrode in the pre-electrolysis stage. Thereafter, in the stripping stage, the potential applied to the working electrode is swept in a direction to cause oxidation (dissolution) of the metal (analyte). By this potential sweeping, when the potential of the working electrode reaches an redox potential of the metal, the metal deposited on the working electrode is rapidly oxidized and dissolved. At this time, a large current flows at the working electrode and is measured to determine the metal ion concentration dissolved in the sample electrolytic solution. Since this stripping method can achieve a low detection limit, it is mainly applied to analysis of a very small amount of heavy metal ions in water, food, or a body fluid (anodic stripping method). In this stripping method, mercury, carbon, and mercury-modified carbon electrodes are used as the working electrodes.

For example, when a mercury electrode is used as a working electrode for analyzing metal ions in pre-electrolysis, the metal ions are reduced while the potential of the working electrode is kept lower than the reduction potential of metal ions. The reduced metal atoms are reacted with mercury on the working electrode to form an amalgam, thereby preconcentrating the metal atoms on the working electrode. Thereafter, in stripping, when the potential of the working electrode is swept to an oxidation side, the metal preconcentrated on the working electrode (amalgam form) is rapidly oxidized at the redox potential of this metal and dissolved.

At this time, the concentration of metal ions can be determined from the measured current flowing through the working electrode (e.g., DENKI KAGAKU SOKUTEI HOU, Akira Fujishima, Masuo Aizawa, and Toru Inoue, Gihodo Shuppan, PP. 206–208).

By using this method, high sensitivity in the pico-mol region is obtained in analysis of lead, zinc, tin, indium ions, etc.

Two other stripping methods were reported. One is a cathodic stripping method. This method is performed by preconcentrating anions such as chloride, bromide, and iodide onto the working electrode and then stripping these anions by sweeping the working electrode potential to the negative potential region which the reduction reaction of anions take place. The other method is an adsorptive stripping method. This method is performed by preconcentrating an analyte on the working electrode whose surface was modified with material which strongly interacts with the analyte, and then stripping the analyte by potential sweeping.

The pulse voltammetry method is a method in which the potential of a working electrode is swept stepwise, e.g., every several mV or several tens of mV in place of linear sweeping of the working electrode potential, and a current flowing through the working electrode is measured by an electrochemical reaction of the analyte is measured immediately after a charging current flowing upon application of a stepwise voltage is attenuated.

This pulse voltammetry method is used when an analyte which cannot be preconcentrated on an electrode by the stripping method is to be detected at a higher sensitivity than that of the lower sweep voltammetry method. The pulse voltammetry method can achieve a sub-$\mu mol$ sensitivity, but its sensitivity is lower than that of the stripping by 100 times or more.

As is well known, the high redox cycling of a redox species occurs upon application of different potentials to two adjacent working electrodes in an electrolytic solution, and a current flowing through the working electrodes can be amplified by 40 times or more (J. Electroanal. Chem. Preliminary note, Vol. 267, P. 291, 1989).

If an interdigital electrode is used as these two working electrodes, a measurement can be performed such that one working electrode of the interdigital electrode is swept and the other working electrode of the interdigital electrode is fixed at a constant potential. Therefore, the measurement almost free from the influence of the charging current can be performed.

When different potentials are applied to the two working electrodes in the interdigital electrode, a lower detection limit of 5 to 10 nmol/l can be obtained quantitatively in the analysis such as a metal (Anal. Chem. Vol. 62, P. 447, 1990).

The problems posed by the above conventional techniques can be summarized as follows. It is difficult for the conventional methods described above to detect an analyte which exits in a solution and hardly be deposited on the electrode after the electrochemical reaction (an oxidation/reduction reaction).

In measurement using the voltammetry method which does not include an analyte deposition on a working electrode in pre-electrolysis, a detection limit of 10 nmol/l to 100 nmol/l is obtained even in the pulse voltammetry method.

In this case, even if a small interdigital electrode capable of increasing the sensitivity is used, only a detection limit of about 5 to 10 nmol/l can be obtained.

This detection limit is higher than that of the stripping voltammetry by one or two order of magnitude.

In the conventional stripping voltammetry, this analysis is performed after electrochemically deposited on an analyte such as metal ions, which is dissolved in a sample solution on a working electrode.

For this reason, the analyte whose solubility is not changed by the redox reaction, and exits in the previous state even after the oxidation/reduction cannot be analyzed.

For example, it is difficult to apply this method to electrochemically reversible biological materials such as hydroquinone (p-dioxybenzene $C_6H_6O$), catechol (o-dioxybenzene $C_6H_6O_2$), catechol amine, NADH, or vitamin $K_3$ (menadione $C_{11}H_8O_2$), and metal complexes such as ferrocene ($C_{10}H_{10}Fe$) derivative, ruthenium hexaamine, or ferrocyanide.

On the other hand, in the case of the adaptive stripping method, it is possible to modify a working electrode with a material which strongly interacts with an analyte and preconcentrates it on the working electrode. Organic molecules may be measured by properly selecting a material (thin film) for modifying the working electrode.

However, a material for modifying the electrode must be selected in accordance with each analyte, and an adsorption state of the analyte in the working electrode is changed in accordance with the ionic strength of the sample electrolytic solution and a slight pH change, thus posing difficult problems for measurement.

SUMMARY OF THE INVENTION

Therefore, a principal object of the present invention is to provide an electrochemical detection method and an apparatus therefor, capable of performing a high-sensitive analysis of a material which exits in a solution after an electrochemical reaction and cannot be deposited on an electrode.

In order to achieve the above object of the present invention, a reference electrolytic solution and a stripping electrode are combined with a sample electrolytic solution for measurement.

Accordingly, the basic concept of the present invention is to use first and second vessels, a reference electrolytic solution stored in the second vessel, closely spaced first and second working electrodes immersed in a sample electrolytic solution for measurement stored in the first vessel, a stripping electrode immersed in the reference electrolytic solution, and an ionic conductor, arranged between the first and second vessel, for electrically connecting the sample electrolytic solution and the reference electrolytic solution. The reference electrolytic solution contains an electrolyte which can be deposited and dissolved reversibly by an electrochemical reaction upon applying a potential to the stripping electrode. The measurement procedures and principle of the present invention are shown as follows. In a first state, after the second working electrode is connected to the stripping electrode, a potential is applied to the first working electrode to deposit the electrolyte dissolved in the reference electrolytic solution on the stripping electrode. In a second state, after the second working electrode is disconnected from the stripping electrode, a potential of the stripping electrode is swept to release the electrolyte from the stripping electrode. The quantitative analysis can be performed by measuring the current flowing through the stripping electrode by the dissolution of the electrolyte in the reference solution.

As described above, when the potential is applied to the first working electrode in the first state wherein the second working electrode is connected to the stripping electrode, self-induced redox cycling occurs between the first working electrode and the second working electrode combined with the stripping electrode. The electrolyte which can be reversibly deposited from the reference electrolytic solution is deposited on the stripping electrode in order to compensate the charge generated on the second working electrode by the self-induced redox cycling.

In the second state, the potential of the stripping electrode is swept. As a result, when the potential of the stripping electrode reaches the redox potential of the electrolyte deposited on the stripping electrode, the electrolyte electrochemically reacts and abruptly dissolves in the reference electrolytic solution, thereby causing a large current flowing. Therefore, the detection of the analyte is performed by measuring the magnitude of the current in the sample electrolytic solution.

BRIEF DESCRIPTION OF THE DRAWINGS

FIG. 1 is a block diagram showing a basic arrangement of an apparatus according to the first embodiment of the present invention;

FIG. 6 is a perspective view showing an arrangement of an electrode unit and a cell of an apparatus according to the fourth embodiment of the present invention;

FIGS. 9A to 9G are sectional views showing a fabrication process of an electrode unit of an apparatus according to the eighth embodiment of the present invention.

DESCRIPTION OF THE PREFERRED EMBODIMENTS

Figure 2:
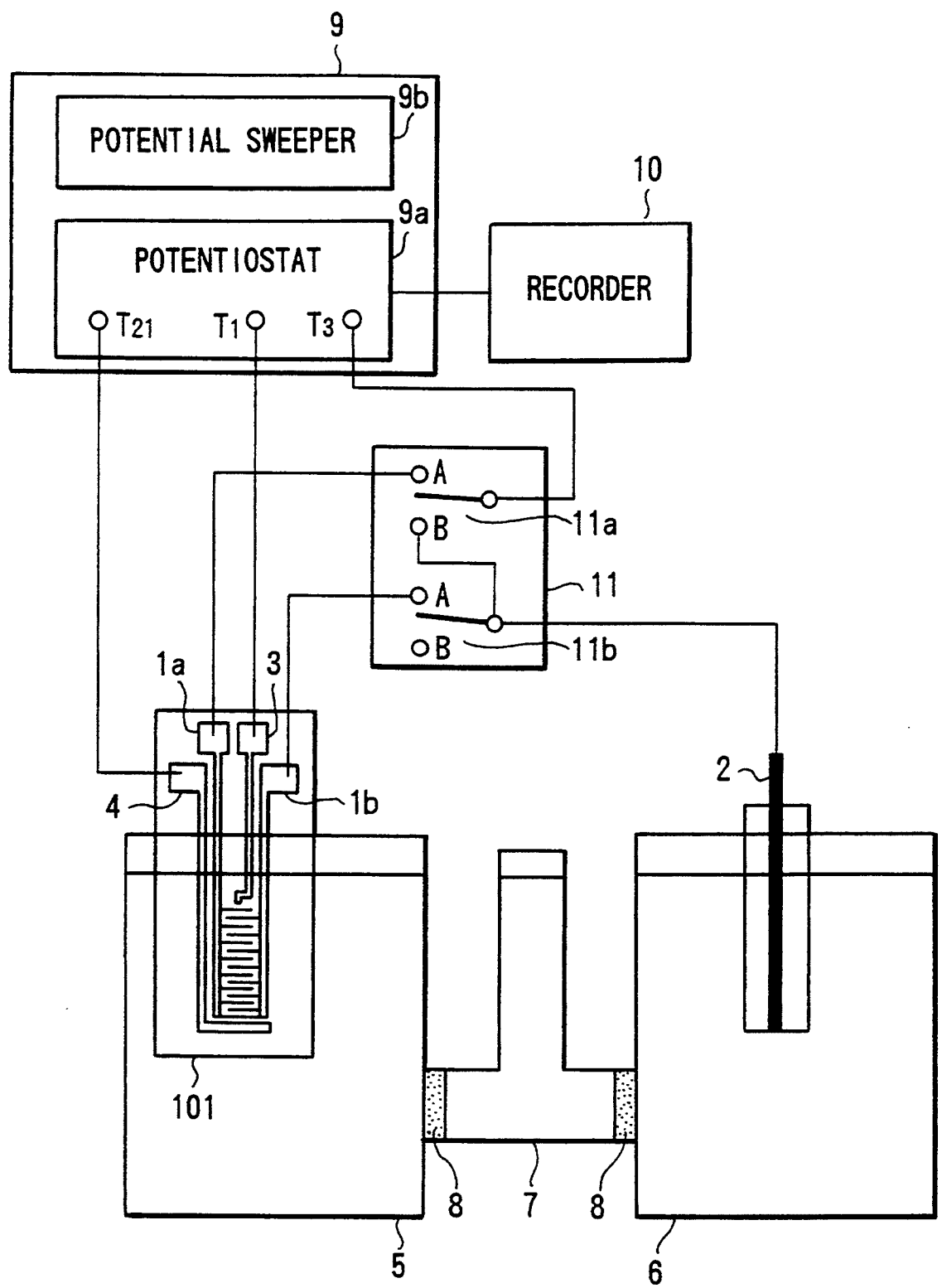
FIG. 2 is a block diagram showing an arrangement of the second embodiment of the present invention.

The present invention will be described with reference to the preferred embodiments thereof.

(First Embodiment)

FIG. 1 shows the basic arrangement of an electrochemical detection apparatus according to an embodiment of the present invention. Referring to FIG. 1, reference numerals 1a and 1b denote opposite working electrodes with a small gap therebetween to constitute an interdigital electrode; 2, a stripping electrode; 3, a reference electrode; 4, an auxiliary electrode; 5, a sample solution vessel in which a sample solution for measurement is stored; 6, an auxiliary solution vessel in which a reference electrolytic solution is stored; 7, a salt bridge having a function of an ionic conductor, arranged between the sample solution vessel 5 and the auxiliary solution vessel 6, for electrically connecting the solutions stored in the vessels 5 and 6; and 8, Vycor glass (high silicate glass) disposed between the salt bridge 7 and the respective vessels. In this embodiment, the working electrodes 1a and 1b, the reference electrode 3, and the auxiliary electrode 4 are immersed in the solution in the sample solution vessel 5. The stripping electrode 2 serves as an electrode on which the material dissolved in the auxiliary solution vessel 6 is deposited and from which the material is dissolved by the potential control. The reference electrode 3 serves as a potential reference. The auxiliary electrode 4 serves as an electrode for smoothly flowing a current in the sample solution for measurement.

The reference electrolytic solution in the auxiliary solution vessel 6 contains a material which can be deposited on the stripping electrode 2 in accordance with the magnitude of a current flowing caused by the electrolysis of the sample solution for measurement and this material can be released by potential control of the stripping electrode 2.

The salt bridge 7 has a structure in which both ends of a small glass tube are closed by the Vycor glass 8 and an electrolytic solution having a high concentration is sealed therein. The salt bridge 7 has a function of electrically connecting the sample solution vessel 5 and the auxiliary solution vessel 6 through the Vycor glass 8 without mixing the solutions stored in the vessels 5 and 6.

Reference numeral 9 denotes a power supply unit for applying potentials to the working electrode 1a, the stripping electrode 2, the reference electrode 3, and the auxiliary electrode; 10, a recorder; and 11, a switch box constituted by two interlocked switches 11a and 11b. In this embodiment, the power supply unit 9 is constituted by a potentiostat 9a and a potential sweeper 9b. A reference electrode terminal T1 of the potentiostat 9a is connected to the reference electrode 3, and an auxiliary electrode terminal T2 of the potentiostat 9a is connected to the auxiliary electrode 4. A working electrode terminal T3 of the potentiostat 9a is connected to a common terminal of the switch 11a of the switch box 11.

When a movable contact connected to the common terminal of the switch 11a of the switch box 11 is connected to the A side, the common terminal is connected to the working electrode 1a. However, when the movable contact is connected to the B side, the common terminal of the switch 11a is connected to the common terminal of the switch 11b and the stripping electrode 2. And when the movable contact connected to the common terminal of the switch 11b is connected to the A side, the common terminal is connected to the working electrode 1b. Note that the B side of the switch 11b is open.

In this switch box 11, in the state wherein the movable contact is connected to the A side, the working electrode terminal T3 of the potentiostat 9a is connected to the working electrode 1a, and at the same time, the working electrode 1b is connected to the stripping electrode 2. On the other hand, in the state wherein the movable contact is connected to the B side, the working electrode terminal T3 of the potentiostat 9a is directly connected to the stripping electrode 2.

The recorder 10 is connected to the potentiostat 9a to detect a voltage (V) between the working electrode terminal T3 of the potentiostat 9a and the reference electrode terminal T1 and to detect a current (A) flowing through the working electrode terminal T3.

The potential sweeper 9b sweeps the potential of the working electrode terminal T3 with reference to the potential of the reference electrode terminal T1 of the potentiostat 9a.

An operation of the electrochemical detection apparatus having the above arrangement will be described below. The operation of the electrochemical apparatus of this embodiment will be basically described in two stages.

The first stage is called pre-electrolysis serving as a stage for depositing on the stripping electrode 2 an electrolyte dissolved in the reference electrolytic solution in the auxiliary solution vessel 6.

The second stage is called stripping for releasing the electrolyte deposited on the stripping electrode 2 to dissolve it in the reference electrolytic solution. In this stripping, a current flowing through the stripping electrode is measured to perform analysis of a material dissolved in the sample solution.

In the pre-electrolysis stage, the movable contacts of the switches 11a and 11b of the switch box 11 are connected to the A sides. A predetermined potential enough to perform oxidation or reduction of analyte in the sample solution is set to the working electrode 1a by the potentiostat 9a. This state continues for a required period of time to perform oxidation and reduction between the working electrodes 1a and 1b. The electrolyte in the reference electrolytic solution deposits on the stripping electrode accompanied with oxidation/reduction of analyte in the sample solution for measurement.

In the stripping stage, the switches 11a and 11b of the switch box 11 are set to the B sides, and the potential of the stripping electrode 2 is swept by the potential sweeper 9b and the potentiostat 9a.

When the potential of the stripping electrode 2 reaches the redox potential of the electrolyte, the electrolyte deposited on the stripping electrode 2 is released and dissolved in the reference electrolytic solution. At this time, a large current flows through the stripping electrode 2. This current is detected by the potentiostat 9a and recorded on the recorder 10.

A peak shaped current is recorded on the recorder 10 when the material deposited on the stripping electrode is released at a predetermined (redox) potential. The magnitude of the peak is proportional to an amount of deposited material which is also proportional to the analyte concentration in the sample solution for measurement.

The above operation will be described in more detail below. In pre-electrolysis, the oxidized/reduced material (the analyte) produced by oxidation/reduction on the working electrode $1a$ in the sample solution diffuses to the working electrode $1b$. Since the oxidized/reduced material (analyte) exists on the working electrode $1b$, a reduction/oxidation reaction of the material occurs and generates charge on the working electrode $1b$. The reduced/oxidized material (analyte) produced on the working electrode $1b$ diffuses back to the working electrode $1a$ and repeat the same reaction as described above. Thus, self-induced redox cycling is established.

During the self-induced redox cycling, the deposition/dissolution material continues to deposit on the stripping electrode 2 immersed in the reference electrolytic solution of the vessel 6 which is electrically connected to the sample solution vessel 5 through the salt bridge. An amount of charge generated during deposition/dissolution material on the stripping electrode 2 corresponds to the amount of charge generated on the working electrode $1b$ connected through the switch box 11. This means that the generated charge on the working electrode $1b$ by the self-induced redox cycling is compensated by the charge generated by the deposition of the deposition/dissolution material.

The self-induced redox cycle phenomenon described above continues as long as sufficient potential that the oxidation/reduction of the analyte takes place is applied to the working electrode $1c$. During this period, the deposition/dissolution material continues to deposit on the stripping electrode 2. This self-induced redox cycle phenomenon was originally found by the present inventors when the working electrode $1a$ was placed very closely to the electrode $1b$ in the sample solution, and another electrode (corresponding to the stripping electrode 2) electrically connected to the electrode $1b$ was placed far from the electrode $1a$ in the same sample solution. This phenomenon was also observed when a microelectrode was placed very closely to the working electrode $1a$ in the sample solution. By applying the potential only to the working electrode $1a$ in the same solution, the current amplification was observed by the similar effect of redox cycling in twin potentiostated electrolysis (e.g., J. Electrochem. Soc., Vol. 138, No. 12, 3549, 1991).

Figure 10:
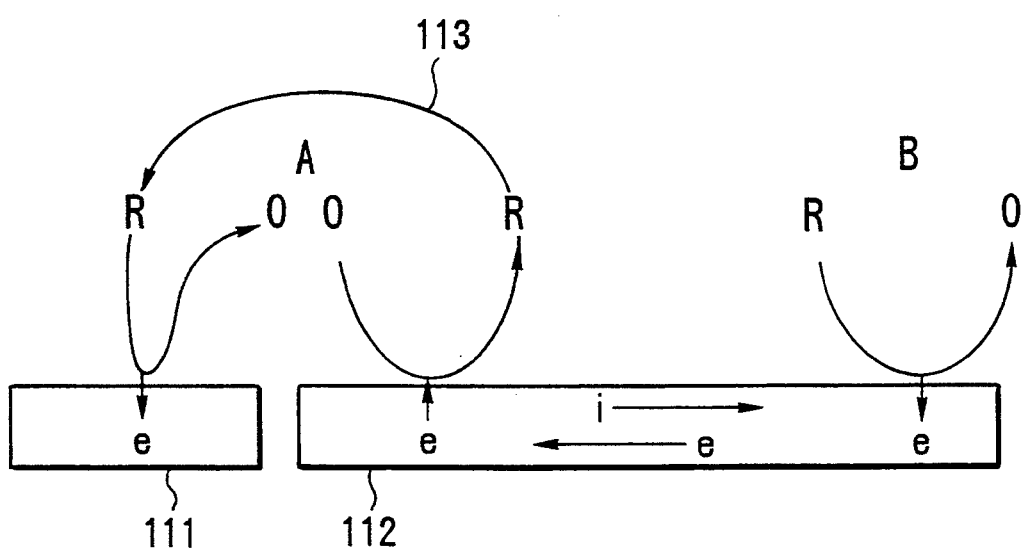
FIG. 10 is a view for explaining the principle of a self-induced redox cycle.

This current amplification is caused by the self-induced redox cycling represented in FIG. 10.

The self-induced redox cycle will be described in more detail with reference to FIG. 10. Referring to FIG. 10, reference numeral 111 denotes a first electrode (corresponding to $1a$ in FIG. 1) connected to a potentiostat; and 112, a second electrode (corresponding to $1b$ in FIG. 1) not connected to the potentiostat. One terminal of the second electrode 112 is located close to the first electrode 111, and the other terminal of the second electrode 112 is spaced apart from the first electrode 111. In this case, the first and second electrodes 111 and 112 are in contact with a solution in which reduced and oxidized materials R and O are dissolved.

When a potential is applied to the first electrode 111, the reduced form R is oxidized and releases an electron to the first electrode 111 by the electrochemical reaction on the first electrode 111. This oxidation reaction induces the concentration difference of the oxidized material O between the point A and the point B. That is, the concentration of the oxidized form O at the point A is higher than that at the point B, and a non-equilibrium state is established.

In the solution, in order to restore an equilibrium state, the oxidized form O diffuses toward the point B. At the same time, electrons flow in the direction of the point A to the point B within the second electrode 112. This is because, at the point B of the second electrode 112, the electrons are released from the reduced form R, so that the reduced form R is converted into an oxidized form O. The released electrons flow in the direction of the point A from the point B within the second electrode 112 and are consumed by the reduction reaction of the oxidized form O at the point A. These electrons are supplied to reduce the oxidized form O.

When this non-equilibrium state of the concentrations of the oxidized form O at the points A and B on the second electrode 112 is formed, an electromotive force is generated that can flow electrons within the second electrode 112.

In general, the electron flow in a metal is much faster than that by natural ionic diffusion of molecules and ions in a solution. For this reason, the reduction of the oxidized form O and the oxidation of the reduced form R at the points A and B in the second electrodes 112 are much more effective than the diffusion of the oxidized form O in the solution to change the concentration of the equilibrium state from that of the non-equilibrium state.

The generation of the oxidized form O continues by oxidizing the reduced form R by applying the potential to the first electrode 111. The generated oxidized form O diffuses to the point A of the second electrode 112. As described above, to restore the non-equilibrium of the oxidized form O on the second electrode 112, the oxidized form O is immediately reduced at the point A of the second electrode 112 and this reduced material R is immediately oxidized by the first electrode 111, thus forming a redox cycle 113.

The redox cycle 113 shown in FIG. 10 is the self-induced redox cycle, thereby amplifying the current of the first electrode 111.

As described above, the deposition/dissolution material which has been continuously deposited in pre-electrolysis by the self-induced redox cycle is released (stripping) at once by sweeping the potential of the stripping electrode 2 upon connecting the movable contacts of the respective switches of the switch box 1 to the B sides. A peak current flowing through the stripping electrode 2 is caused by releasing this deposition/dissolution material at once.

This peak current is proportional to the amount of deposition/dissolution material deposited on the stripping electrode 2. The amount of deposition/dissolution material is proportional to the product of the analyte concentration in the sample solution and the pre-electrolysis time, so that the analyte concentration in the sample solution can be quantitatively measured.

In this invention, the self-induced redox cycling in the sample solution and the deposition reaction of the deposition/dissolution material on the stripping electrode 2 in the auxiliary solution vessel 6 are basic operations. The amount of deposition/dissolution material deposited on the stripping electrode 2 is proportional to the product of the pre-electrolysis time and the analyte concentration in the sample solution. Therefore, even if the analyte concentration is low, a large detection current can be obtained by prolonging the pre-electrolysis time, thereby greatly improving the detection limit of the analyte dissolved in the sample solution.

The working electrodes 1a and 1b have a form of small paired electrodes such as a small interdigital array electrode, small paired band electrodes, or small ring-disk electrodes. Examples of the metal material for forming these electrodes are gold, platinum, silver, copper, palladium, chromium, titanium, and stainless steel. P- or n-type silicon, p- or n-type germanium, cadmium sulfide (CdS), titanium dioxide ($TiO_2$), zinc oxide (ZnO), gallium phosphide (GAP), gallium arsenide (GaAs), indium phosphide (InP), cadmium selenide (CdSe), cadmium telluride (CdTe), molybdenum disulfide ($MoS_2$), tungsten selenide (WSe), cuprous oxide ($Cu_2O$), tin oxide ($SnO_2$), indium oxide ($In_2O_3$), and indium-tin oxides may be used as materials for the working electrodes. Semi-metallic materials such as glassy carbon, a conductive carbon paste, or a conductive carbon film may also be used as a material for the working electrodes.

In recent years, extensive studies have been made on microelectrodes for analyzing a small area in a living body or a small amount of solution sample, and these electrodes have been used in a variety of applications such as a sensor or a measurement of a very small amount of material in a living cell. Most of the microelectrodes are used such that metal wires as of platinum or gold or carbon fibers are sealed in a thin glass tube. The response of this microelectrode depends on its shape. When the electrode size is reduced, the response speed and the S/N ratio are increased. Since high-sensitivity can be obtained by reducing the electrode size in principle, various shapes of electrodes and their miniaturization have been examined. However, when the electrode diameter reduces to about 1 μm, a current to be detected is reduced below nA order. It is therefore difficult to perform measurement due to the external noise in actual measurement.

For this reason, it is proposed to increase (formation of an array) the number of microelectrodes so as to increase an absolute current value while keeping the high current density of the microelectrodes and their high S/N ratio to a charging current. As a method of fabricating an array of microelectrodes, lithographic techniques have been recently used. A large number of microelectrodes having an arbitrary shape can be fabricated on a substrate with good reproducibility.

As a method of fabricating an array of working electrodes which are insulated with small gaps of the micron or submicron order each other, photolithography is combined with micropatterning techniques such as dry-etching, lift-off, and ion-milling methods. Alternatively, a method of setting a needle-like microelectrode close to a conductor using a scanning tunnel microscope (STM), or a method of facing two opposite electrodes with a small distance using a micrometer or an appropriate spacer is available.

Examples of the material for the stripping electrode connected to one of the paired microelectrodes are a dropping mercury electrode, an amalgam electrode of mercury and a metal (e.g., gold), a mercury-plated carbon electrode, an HOPG electrode, a carbon fiber electrode, a glassy carbon electrode, a silver electrode, and a carbon paste electrode. Also, electrodes modified with anionic polymers such as Nafion (available from Dupont), polyester sulfonic acid (available from Eastman Kodak), polyvinyl sulfonic acid, or polystyrene sulfonic acid, electrodes modified with cationic polymers (e.g., polydimethyldilaurylammonium chloride, or poly-4-vinyl pyridine), conductive polymers (e.g., polypyrrole, polythiophene, polyaniline, or polyazulene), or derivatives thereof can be used as the materials for the stripping electrodes.

Examples of the salt bridge 7 for connecting the sample solution vessel 5 and the auxiliary solution vessel 6 are a salt bridge which comprises a thin glass or plastic tube filled with an ionic conductor obtained by dissolving an electrolyte such as potassium chloride or potassium nitrate in an agar is sealed in the thin glass or plastic tube, a salt bridge which comprises a high concentrated electrolytic solution filled in a glass or plastic tube whose ends sealed with porous glass or the like having a low liquid permeability, a ceramic ionic conductor, its thin film, a polymeric ionic conductor, and its thin film.

Examples of the electron conductor for connecting the working electrode 1b to the stripping electrode 2 through the switch box 11 are a metal wire, a metal thin film, a conductive carbon rod, a conductive carbon thin film, and an electron conductive polymer.

The reference electrode may be located in the first or second vessel or in the salt bridge, so far as the same results as in the first embodiment can be obtained. The auxiliary electrode may also be located in the first or second vessel or in the salt bridge so far as the same results as in the first embodiment can be obtained. The reference and auxiliary electrodes need not be located at the same position.

An embodiment for analyzing ruthenium hexaamine at a very low concentration by the electrochemical detection apparatus of the present invention having the above arrangement will be described below.

(Second Embodiment)

In this embodiment, paired working electrodes 1a and 1b are constituted by a gold interdigital array electrode, and a stripping electrode 2 is constituted by a disk glassy carbon electrode having a diameter of 3 mm. Ruthenium hexaamine is used as an analyte because it exists as an oxidized form in a solution and has electrochemical reversibility. This sample cannot be measured by a conventional stripping method.

Figure 3:
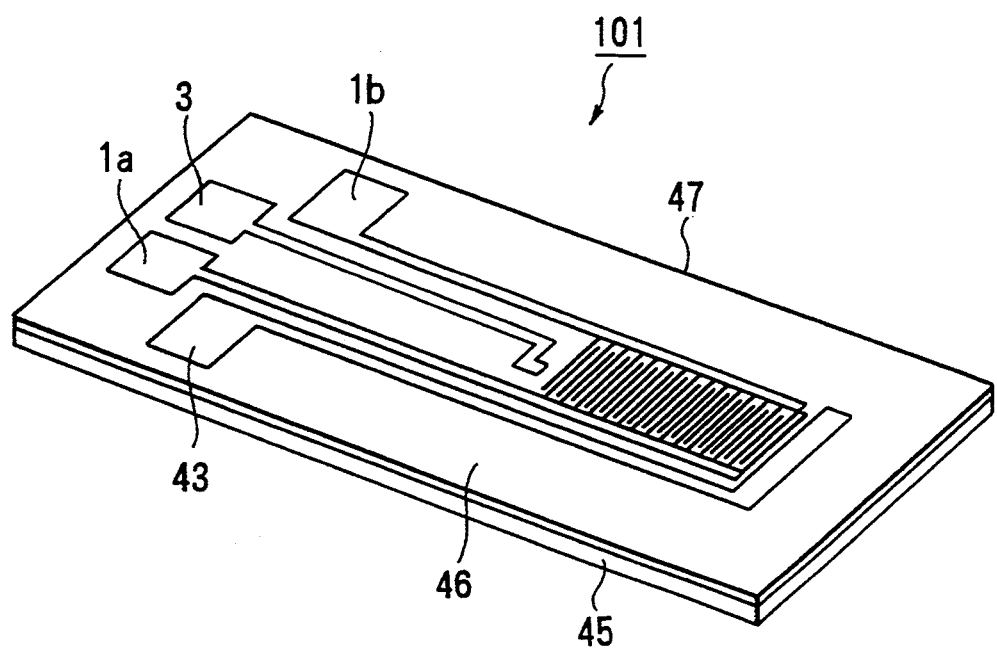
FIG. 3 is a perspective view showing an electrode unit of an electrochemical detection unit according to the second embodiment of the present invention.

FIG. 2 shows an arrangement of an electrochemical detection apparatus of this embodiment. FIG. 3 shows a structure in which the working electrodes 1a and 1b constituted by an interdigital array electrode, a reference electrode 3, and an auxiliary electrode 43 are formed on a single substrate. Referring to FIG. 2, reference numeral 101 denotes a detection electrode unit in which the working electrodes 1a and 1b, the reference electrode 3, and an auxiliary electrode 4 are integrated on the single substrate. Any other arrangement of the second embodiment is the same as that of FIG. 1, and a detailed description thereof will be omitted.

Referring to FIG. 3, the detection electrode unit 101 comprises the reference and auxiliary electrodes 3 and 43 which are in contact with the sample solution, and the working electrodes 1a and 1b obtained by arranging an interdigital array electrode 47 with a small gap, which all the electrodes are formed on an insulating oxide film 46 formed on a silicon substrate 45. The detection electrode unit 101 is fabricated by known lithographic techniques such as formation of an electrode pattern using a resist on the insulating oxide film 46, deposition of an electrode material by sputtering, deposition of an insulating film by plasma CVD, and exposure of a portion serving as an electrode by reactive ion etching.

The interdigital array electrode 47 is composed of two series comb-like electrodes (1a and 1b) used in this embodiment. The widths of the two comb-like electrodes were both 2 μm, and their length was 2 mm, The gap and the number of pairs of electrodes were 2 μm and 750, respectively. An electrode material is a gold-/titanium film. The distal end portion of the reference electrode 3 is plated with silver to improve the function as the reference electrode. A salt bridge 7 is obtained such that both ends of a small glass tube are closed with Vycor glass and the glass tube is filled with a saturated potassium nitrate solution.

The two working electrodes 1a and 1b of the detection electrode unit 101, and the stripping electrode 2 and a working electrode terminal T3 of a potentiostat 9a (HECS972 available from Huso) are connected to a switch box 11 having the same basic arrangement and function as those in FIG. 1. The reference electrode 3 and the auxiliary electrode 4 of the detection electrode unit 101 are connected to a reference electrode terminal T1 and an auxiliary electrode terminal T21 of the potentiostat 9a, respectively.

An analysis of a low concentration of ruthenium hexaamine using the apparatus having the arrangement as described above will be described below.

A sample solution was a pH 4.2 standard buffer solution (available from Nakarai Chemicals LTD.) containing 1 μmol/l of ruthenium hexaamine. The auxiliary solution was an electrolytic solution containing 0.1 mol/l of potassium nitrate (KNO$_3$) and 1 μmol/l of silver nitrate.

As previously described, this analysis is performed in two stages.

In pre-electrolysis as the first stage, switches 11a and 11b of the switch box 11 were set on the A sides, and the potential of the working electrode 1a of the detection electrode unit 101 was held at −0.4 V. Electrolysis of ruthenium hexaamine continued for 10 minutes. During this period, the auxiliary solution was kept stirring. After pre-electrolysis, stirring of the auxiliary solution was immediately stopped. The resultant solution was left for 10 seconds, until the solution became still.

The second stage was then immediately started.

In the stripping operation as the second stage, the switches 11a and 11b of the switch box 11 were set to the B sides, and the potential of the stripping electrode 2 was swept from −0.4 V to 0.5 V at a scan rate of 20 mV/sec.

By the above operations, a peak current of 7 μA caused by the oxidation (dissolution) of silver from the stripping electrode 2 was observed at a potential of 0.35 V on a recorder 10.

Even if cyclic voltammogram of ruthenium hexaamine was obtained using this working electrode 1a, ruthenium hexaamine could not be observed due to the background current from dissolved oxygen. The maximum theoretical value of a detection current at this type of working electrode can be calculated as 8 nA. Therefore, according to the present invention, a signal can be amplified to about 875 times. And a sample having a lower concentration can be measured. Although a similar measurement was performed for an electrolyte which did not contain ruthenium hexaamine, no peak current was observed.

The results at the analysis of ruthenium hexaamine performed by decreasing the concentration of ruthenium hexaamine in using the same apparatus as described above are summarized in Table 1. The above result (sample 1) is also summarized in Table 1.

TABLE 1

Variation of Peak Current and Gain as a Function of Ruthenium Hexaamine Concentration

| Sample | Concentration (nmol/l) | Peak Current (μA) | Gain |
|---|---|---|---|
| 1 | 1000 | 7.0 | 880 |
| 2 | 100 | 2.6 | 3250 |
| 3 | 10 | 0.28 | 3500 |
| 4 | 1 | 0.03 | 3750 |

The gain of sample 1 was low due to a broad stripping peak when the concentration of ruthenium hexaamine is high, however, a sharp peak appeared with a decrease in concentration, thereby increasing the gain, as shown in Table 1.

As described above, according to the present invention, a low concentration analyte which cannot be detected by the conventional stripping method can be measured with a high sensitivity.

(Third Embodiment)

As the third embodiment, a stripping analysis of a low concentration of ruthenium hexaamine as a sample solution will be described with reference to FIG. 4. A micro disk array electrode embedded in a surface electrode (MDAS) is used as a working electrode, and a glassy carbon electrode is used as a stripping electrode 2.

Figure 4:
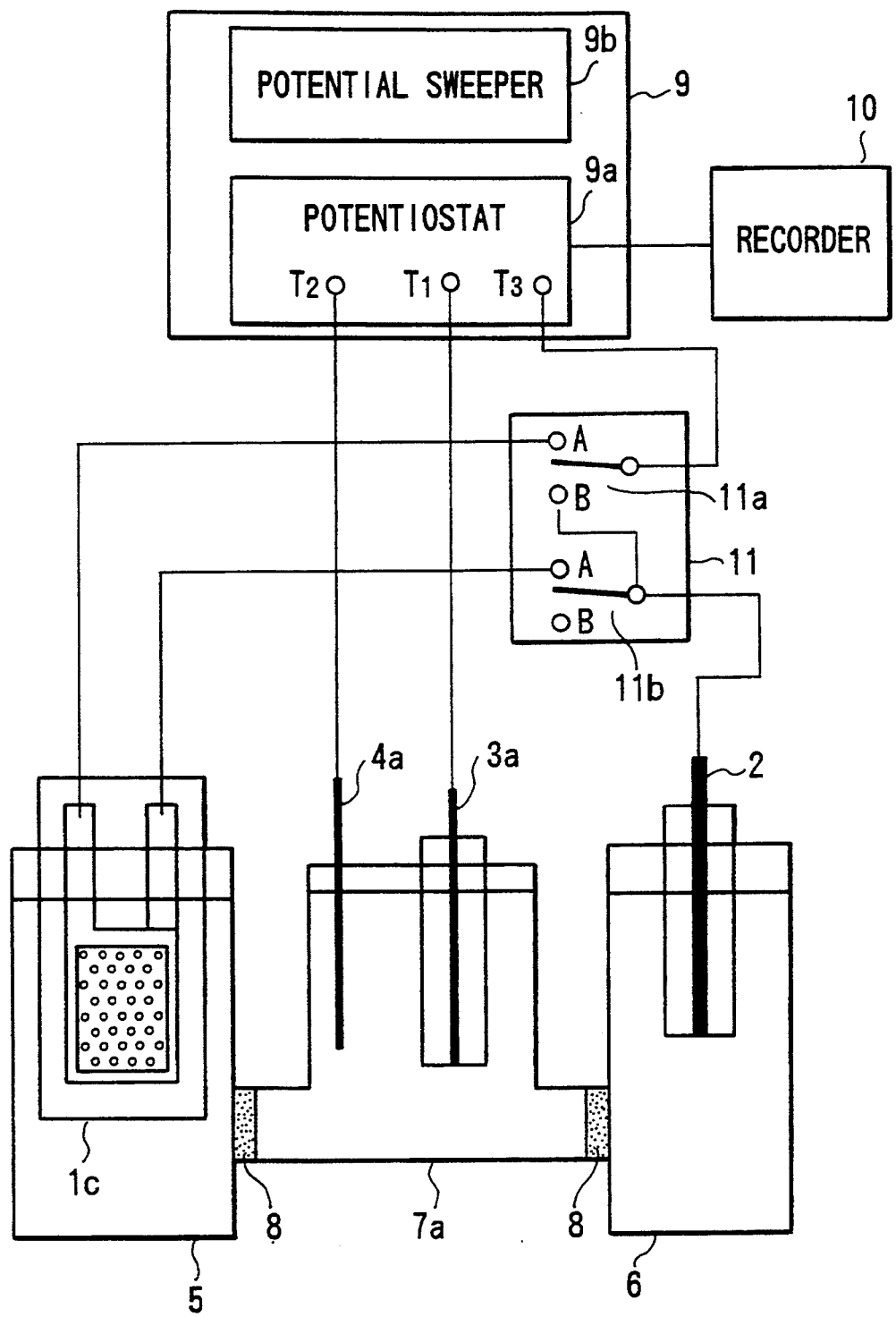
FIG. 4 is a block diagram showing an arrangement of an apparatus according to the third embodiment of the present invention.

Referring to FIG. 4, reference numeral 1c denotes a detection electrode similar to the pair of working electrodes 1a and 1b (FIG. 1) constituted as a micro disk array electrode embedded in a surface electrode; 3a, an Ag/AgCl reference electrode; and 4a, a Pt auxiliary electrode. The reference electrode 3a and the auxiliary electrode 4a are immersed in an electrolytic solution in a salt bridge 7a. Any other arrangement is the same as that in FIG. 1.

Figure 5:
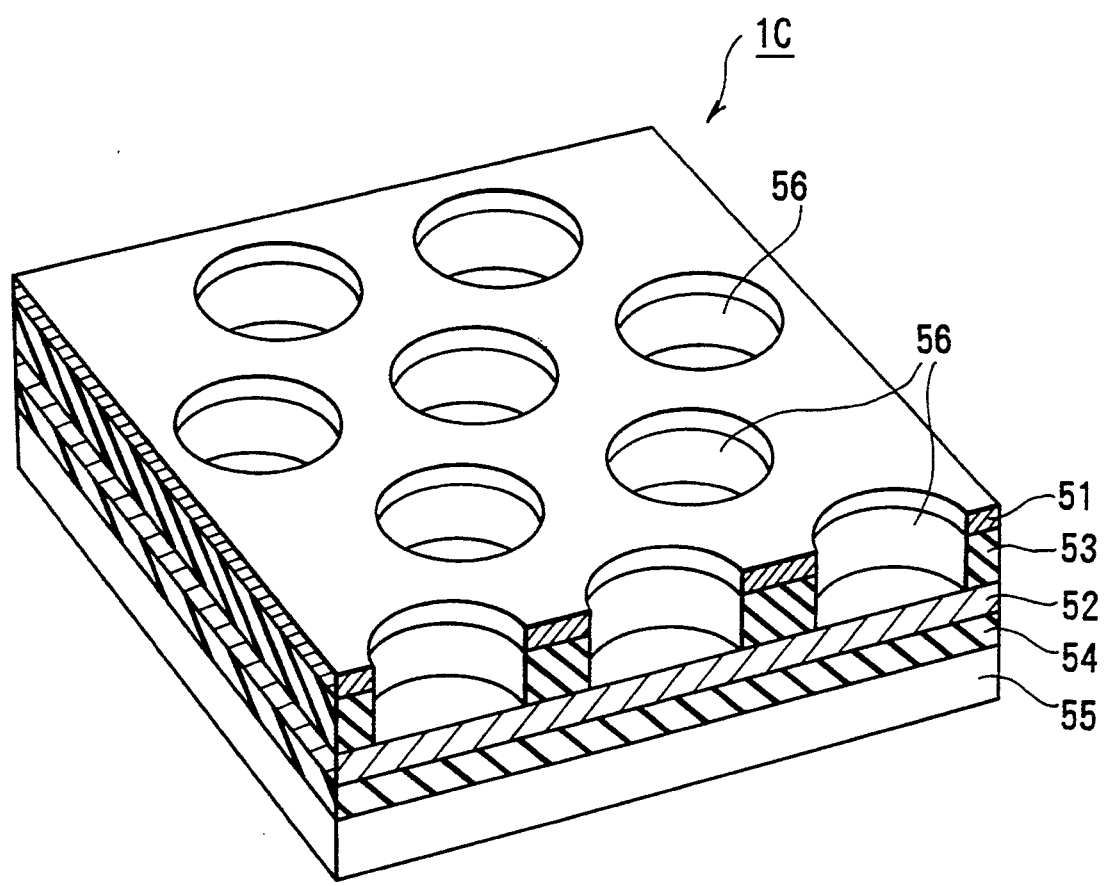
FIG. 5 is a perspective view showing an arrangement of a detection electrode having a micro disk array electrode embedded in a surface electrode structure of the third embodiment.

FIG. 5 shows part of the structure of the detection electrode 1c. Referring to FIG. 5, reference numeral 51 denotes an Au/Ti surface electrode; 52, an Au/Ti micro disk array electrode layer; 53 and 54, silicon dioxide insulating layers; and 55 a silicon substrate. A micro disk array electrode layer 52, the insulating layer 53, and the surface electrode 51 are sequentially stacked on the silicon substrate 55 having the insulating layer 54 by sputtering, and micro disk array electrode 56 is formed by a photographic technique and reactive ion etching or the like, thereby forming the detection electrode 1c. In this embodiment, the detection electrode 1c has a size of 8 mm$^2$, and has about 407,500 micro disk electrodes. A diameter of each micro disk electrode is 10 μm.

An analysis of a very small amount of ruthenium hexaamine using the electrochemical detection apparatus shown in FIG. 4 will be described below.

In this embodiment, a sample solution for measurement was a pH 4.2 standard buffer solution containing 1 μmol/l of ruthenium hexaamine. The auxiliary solution was an electrolytic solution containing 0.1 mol/l of potassium nitrate and 1 μmol/l of silver nitrate.

In pre-electrolysis as the first stage, switches 11a and 11b of the switch box 11 were set on the A sides, and the potential of the micro disk array electrode 52 (FIG. 5) of the detection electrode 1c was held at −0.4 V. Electrolysis of ruthenium hexaamine continued for 5 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the switches 11a and 11b of the switch box 11 were set to the B sides, and the potential of the stripping electrode 2 was swept from −0.4 V to 0.5 V at a scan rate of 20 mV/sec.

By the above operations, a peak current of 25.8 μA based on oxidation (dissolution) of silver from the stripping electrode 2 was observed at a potential of 0.35 V on a recorder 10. Even if cyclic voltammogram of ruthenium hexaamine was obtained using this detection electrode 1c, the current of ruthenium hexaamine could not be observed due to the background current from dissolved oxygen. The maximum theoretical value of a detection current of this working electrode can be calculated as 200 nA. According to the present invention, a signal can be amplified to about 128 times, which enables to measure a sample having a lower concentration. Although a similar measurement was performed for an electrolyte which did not contain ruthenium hexaamine, no peak was observed.

As described above, according to the present invention, a sample having a low concentration can be measured with a high sensitivity as in the first embodiment where the micro disk array electrode embedded in the surface electrodes is used as the detection electrode 1c.

(Fourth Embodiment)

As the fourth embodiment, a stripping analysis of a low concentration of potassium ferrocyanide as a sample solution will be described on the basis of an electrochemical detection apparatus shown in FIG. 6. An Au interdigital array electrode, and an Au stripping electrode 2a formed on a single substrate are used in this embodiment. Potassium ferrocyanide is suitable as a standard sample due to the same reason as ruthenium hexaamine.

Following the same procedures as in the first embodiment, a detection electrode unit 101a having a small interdigital array electrode 47a, an auxiliary electrode 4, a reference electrode 3, and the stripping electrode 2a is formed on a single substrate. The interdigital digital electrode 47 is composed of two series comb-like electrodes (1a and 1b) used in this embodiment. The widths of the two comb-like electrodes were both 2 μm, and their length was 2 mm. The gap and the number of pairs of electrodes were 2 μm and 750, respectively. The stripping electrode 2a has a rectangular shape having a size of 2 mm×3.5 mm. The total electrode area is 1 cm×3 cm. The interdigital electrode 47a, the stripping electrode 2, and terminals of the respective electrodes are arranged, as shown in FIG. 6. These electrodes are formed by, e.g., photolithographic techniques.

The electrochemical detection apparatus is fabricated by adhering the electrode unit 101a to the bottom surface of a pyrex cell frame 64 (available from Corning Glass Works) with an epoxy adhesive resin. The cell frame 64 has a size of 1 cm×2 cm×1 cm, and has two square through holes, and 1 mm-thick Vycor glass 8 is incorporated in the partition wall between the two holes of the cell frame 64. In this case, the cell 64 is partitioned into a sample solution compartment 64a and an auxiliary solution compartment 64b. The reference electrode 3, the auxiliary electrode 4, and the interdigital array electrode 47a are arranged in the sample solution compartment 64a, and the stripping electrode 2a is arranged in the auxiliary solution compartment 64b. The partitioning component between the sample solution compartment 64a and the auxiliary solution compartment 64b is constituted by a salt bridge 7, so that these compartments can be electrically connected to each other. Although not shown in FIG. 6, all the electrodes are connected to a switch box having two switches and a potentiostat as in the first embodiment.

As described above, the small cell 64 partitioned by the Vycor glass 8 is mounted on the electrode unit 101a. An analysis of a very small amount of potassium ferrocyanide will be described below using the cell 64 (FIG. 6) as the vessels for the sample solution and the auxiliary solution.

The sample solution for measurement used herein was a pH 4.2 standard buffer solution containing 1 μmol/l of potassium ferrocyanide and was filled in the cell (sample solution compartment) 64a (corresponding to the sample solution vessel 5 in FIG. 1) having the interdigital array electrode 47a at the bottom of the compartment. The auxiliary solution was an electrolytic solution containing 0.1 mol/l of potassium nitrate and 1 μmol/l of silver nitrate and was filled in the cell (auxiliary solution compartment) 64b (corresponding to the auxiliary solution vessel 6 in FIG. 1) having the stripping electrode 2 at its bottom.

Operations of this embodiment are performed in two stages as in the previous embodiments.

In pre-electrolysis as the first stage, switches were set on the A sides, and the potential of one detection electrode (working electrode) of the interdigital array electrode 47a was held at −0.4 V. Electrolysis of potassium ferrocyanide continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the switches were set to the B sides, and the potential of the stripping electrode 2 was swept from −0.4 V to 0.5 V at a scan rate of 20 mV/sec.

By the above operations, a peak current of 0.1 μA caused by oxidation of silver was observed at a potential of 0.35 V on a recorder.

A cyclic voltammogram of potassium ferrocyanide using one of the working electrodes of the interdigital array electrode 47a exhibited a peak current of 2 nA. Because of this 50 times signal amplification by the present invention, a much lower concentration sample can be measured. Although a similar measurement was performed for an electrolyte which did not contain potassium ferrocyanide, no peak current was observed.

The solution volume can also be reduced in this embodiment. Even if a sample solution for measurement is a very low volume and a low concentration, high-sensitive measurement can be performed. The arrangement of this embodiment provides advantages in that realizing a smaller electrochemical detection apparatus, and decreasing the amount of sample solution. Integration of electrodes on a single substrate is able to shorten the length of an ionic conductor (salt bridge) which connects the two solution vessels. The resistance of the ionic conductor can be reduced. As a result, reduction in the sensitivity can be prevented.

(Fifth Embodiment)

As the fifth embodiment of the present invention, a carbon/platinum interdigital array electrode and a carbon/platinum stripping electrode 2 are formed on the same substrate, and an analysis of a trace amount of ruthenium hexaamine using these electrodes will be described below.

The platinum layer under the carbon layer can improve a total conductivity of the electrode material. The electrochemical measurement can be advantageously performed. The carbon electrode can be widely used in electroanalytical method because of a wide potential window.

The electrode fabrication process will be described with reference to FIGS. 7A to 7H.

Figure 7A:
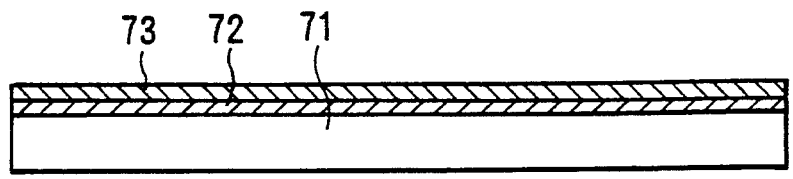
FIGS. 7A to 7H are sectional views showing a fabrication process of electrodes of an apparatus according to the fifth embodiment of the present invention.

As shown in FIG. 7A, a silicon wafer 71 (available from Osaka Titanium Co., Ltd.) having a 1-$\mu$m thick $SiO_2$ layer 72 was placed at a predetermined position in a sputtering apparatus (SPF332H available from Anelva). Titanium and platinum were sputtered at 50W for one minute and 70W for 3.5 minutes, respectively, while the substrate was rotated in an argon atmosphere at a pressure of 1.3 Pa, thereby forming a 100-nm thick platinum/titanium thin film 73.

Figure 7B:
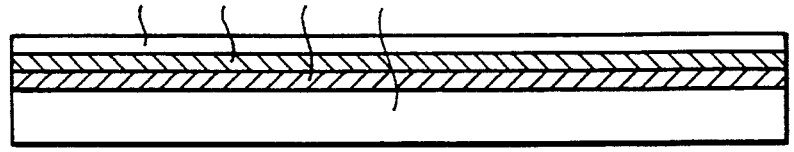

1 g of 3,4,9,10-perylenetetracarboxylic dianhydride (PTDA) in a quartz boat was placed in an end portion of a 80-cm long quartz tube, and the boat was covered with a quartz glass wool. The silicon substrate 71 was placed at the center of the quartz tube, and the tube was evacuated to a pressure of 0.1 Torr. Two heaters were mounted on the tube. By these heaters, the silicon substrate 71 was heated to 1,000° C., and the temperature of the PTDA in the quartz boat was increased to 450° C. The PTDA was sublimed to perform deposition on the silicon substrate 71 for 15 minutes. A carbon thin film 74 was formed on the platinum/titanium thin film 73 on the silicon substrate 1 (FIG. 7B).

The quartz tube was removed from an electrical furnace and was cooled naturally. The vacuum state was broken to an atmospheric state to remove the silicon substrate 71 from the quartz tube. A silicon-based positive resist was spin-coated on the carbon thin film 74 at 4,000 rpm for 40 seconds and was prebaked at 90° C. for 90 seconds.

Figure 7C:
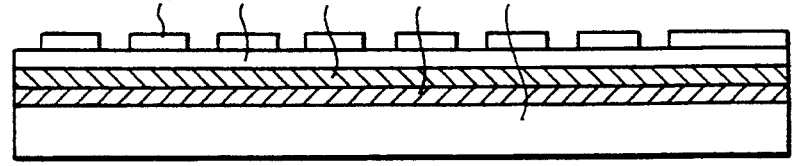
Figure 7D:
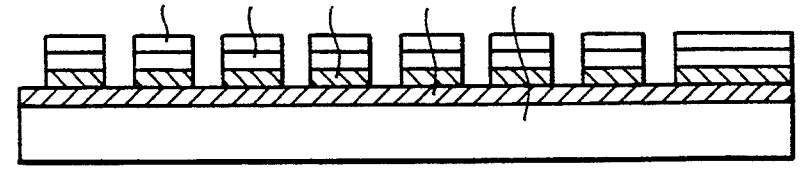
Figure 7E:
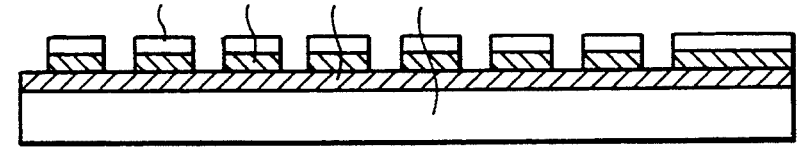

The wafer with the resist was exposed with a stepper (NSR-1010G available from Nikon) through a photomask and developed in an NMD-W developer (available from Tokyo Ohka) to form a resist pattern 75, as shown in FIG. 7C.

The silicon substrate 1 having the resist pattern 75 thereon was placed in a reactive ion etching apparatus (DEM451 available from Anelva), and a carbon film area which was not covered with the resist pattern 75 was etched to transfer the resist pattern 75 to the carbon thin film 74.

The underlying platinum/titanium film was etched with argon ion milling (FIG. 7D), and then the resist pattern 75 was removed to form a carbon/metal composite interdigital array electrode (FIG. 7E) having the same shape as in the fourth embodiment (FIG. 6). Although not shown, any other electrode such as a stripping electrode was formed together.

Figure 7F:
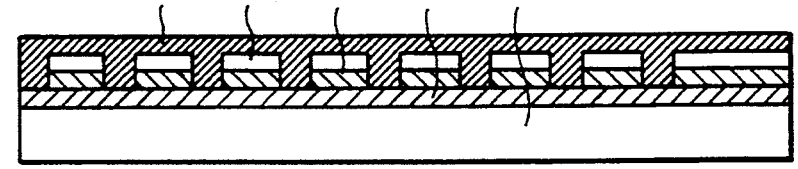

As shown in FIG. 7F, the wafer having this electrode was placed in a plasma CVD apparatus (AMP3300 available from Applied Material) to form a 250-nm thick silicon nitride film 76.

Figure 7G:
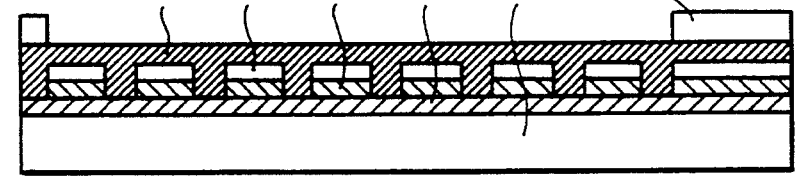

A resist (TSMR-V3 available from Tokyo Ohka) was spin-coated on the entire surface of the resultant wafer at 4,000 rpm for 40 seconds. The resultant wafer was prebaked at 90° C. for 90 seconds. The prebaked wafer was exposed, developed and rinsed to obtain a pattern 77 (FIG. 7G).

Figure 7H:
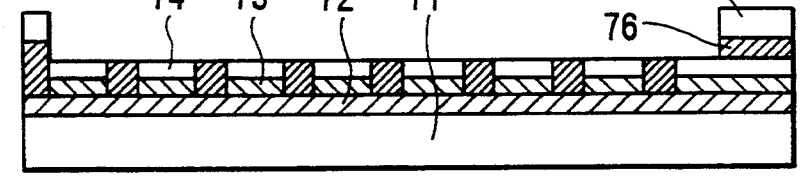

The silicon substrate 71 having the pattern 77 thereon was placed in a reactive ion etching apparatus, and the silicon nitride film 76 was etched until the carbon film was exposed in a $CF_4$ gas plasma. As shown in FIG. 7H, the electrodes were insulated from each other.

The width and gap of the comb-like electrode of the resultant interdigital electrode were 2 $\mu$m, and their length was 2 mm, The number of pairs were 50. The stripping electrode had a rectangular shape having a size of 2 mm $\times$ 3.5 mm.

The reference electrode of this electrode unit was connected to a potentiostat and was immersed in a 70° C. silver plating aqueous solution. Two silver wires were used as reference and auxiliary electrodes. Sliver was plated at a current of 2 $\mu$A for 10 seconds.

The resultant electrode unit was adhered to a cell as in the fourth embodiment to obtain an electrochemical detection apparatus.

An analysis of a trace amount of ruthenium hexaamine using this detection apparatus will be described below.

All the electrodes of the electrochemical detection apparatus were connected to a switch box 11 as in the first embodiment and to a potentiostat 9a and a potential sweeper 9b. A pH 4.2 standard buffer solution (available from Nakarai Chemicals LTD.) containing 1 $\mu$mol/l of ruthenium hexaamine was filled in one compartment having the interdigital array electrode, and an electrolytic solution containing 0.1 mol/l of potassium nitrate and 1 $\mu$mol/l of silver nitrate was filled in the other compartment having the stripping electrode.

Operations of this embodiment were performed in two stages as in the previous embodiments.

In pre-electrolysis as the first stage, the switches of the switch box 11 were kept set to the A sides (FIG. 1), and one working electrode of the interdigital array electrode was potentiostated at $-0.4$ V. Electrolysis of ruthenium hexaamine continued for 10 minutes. During this period, the auxiliary solution was kept stirring. After the pre-electrolysis, stirring of the auxiliary solution was stopped. The resultant solution was left for 10 seconds, until the solution became still. The second stage was then immediately started.

In the stripping operation as the second stage, the switches of the switch box 11 were set to the B sides (FIG. 1), and the potential of the stripping electrode was swept from $-0.4$ V to 0.5 V at a scan rate of 20 mV/sec.

By the above operations, a peak current of 0.48 $\mu$A caused by dissolution of silver was observed at a potential of 0.35 V on a recorder 10. A reduction waveform of the ruthenium hexaamine cannot be observed by a cyclic voltammogram using one of the working electrodes in the interdigital array electrode due to a background current from dissolved oxygen. The theoretical current value of this type of working electrode can be calculated as 0.68 nA. In this embodiment, a signal could be amplified to about 700 times, and a trace amount of electrochemically reversible redox species can be measured. Although a similar measurement was performed for an electrolyte which did not contain ruthenium hexaamine, no peak was observed.

(Sixth Embodiment)

As the sixth embodiment of the present invention, a carbon interdigital array electrode and a carbon stripping electrode are formed on the same substrate, and an analysis of a trace amount of ruthenium hexaamine using these electrodes after activating the stripping electrode will be described below.

The electrode of this embodiment does not have the lower metal films 73 of FIG. 7 in the electrode structure of the fifth embodiment. With this structure, even if a high potential is applied to the electrode in a solution, an electrode material will not be eluted. When the electrode surface was activated, an amount of deposited material on the stripping electrode can be increased, thereby advantageously performing a stripping analysis.

1 g of 3,4,9,10-perylenetetracarboxylic dianhydride (PTDA) in a quartz boat was placed in an end portion of a 80-cm long quartz tube, and the boat was covered with a 1-cm thick quartz glass wool.

A silicon wafer with a 1-μm thick $SiO_2$ film was placed at the center of the quartz tube, and the tube was evacuated to a pressure of 0.1 Torr. Two heaters were mounted on the tube.

By these heaters, the silicon substrate was heated to 1,000° C., and the PTDA in the boat was heated to 450° C. The PTDA was sublimed to perform deposition on the silicon substrate for 15 minutes to form a carbon thin film.

The quartz tube was removed from an electrical furnace and was cooled naturally. The vacuum state was broken to an atmospheric state to remove the silicon substrate from the quartz tube.

A silicon-based positive resist was spin-coated on the carbon thin film at 4,000 rpm for 40 seconds and was prebaked at 90° C. for 90 seconds.

The wafer with the resist was exposed with a stepper (NSR-1010G available from Nikon) through a photomask, and the wafer was developed with an NMD-W developer to obtain a pattern.

The silicon substrate having the resist pattern thereon was placed in a reactive ion etching apparatus, and a carbon film area which was not covered with the resist pattern was etched to transfer the resist pattern to the carbon film.

The resist pattern was removed to obtain the respective electrode patterns of the electrode unit having the same shape as that of the fourth embodiment.

A resist (TSR-V3 available from Tokyo Ohka) was spin-coated on the entire surface of the resultant wafer at 4,000 rpm for 40 seconds. The resultant wafer was prebaked at 90° C. for 90 seconds. The prebaked wafer was exposed with a stepper. The exposed wafer was developed with an NMD-W developer to obtain a pattern. The resultant substrate was baked at 200° C. for 30 minutes to convert the resist to an insulator. The width and gap of the comb-like electrode of the interdigital array electrode were 2 μm and the length was 2 mm. The interdigital array electrode had 50 microband pairs. The stripping electrode had a rectangular shape having a size of 2 mm×3.5 mm.

The reference electrode of this electrode unit was connected to a potentiostat and was immersed in a 70° C. silver plating aqueous solution together with a silver wire (reference electrode) and another silver wire serving as the auxiliary electrode. Sliver plating was performed at a current of 2 μA for 10 seconds on a reference electrode. The resultant electrode structure was adhered to a cell as in the fourth embodiment to obtain an electrochemical detection apparatus.

An analysis of a trace amount of ruthenium hexaamine using this detection apparatus will be described below.

0.1 mol/l of sulfuric acid was filled in the auxiliary compartment, a silver/silver chloride reference electrode and an auxiliary electrode were mounted in the auxiliary compartment, and the stripping electrode was activated at 1.8 V for 5 minutes. All the electrodes of the electrochemical detection apparatus were then connected to a switch box 11 as in the first embodiment, and to a potentiostat 9a and a potential sweeper 9b.

A pH 4.2 standard buffer solution (available from Nakarai Chemicals LTD.) containing 1 μmol/l of ruthenium hexaamine was filled in one compartment having the interdigital array electrode, and an electrolytic solution containing 0.1 mol/l of potassium nitrate and 1 μmol/l of silver nitrate was filled in the other compartment having the stripping electrode.

Operations of this embodiment were performed in two stages as in the previous embodiments.

In pre-electrolysis as the first stage, the switches of the switch box 11 were set to the A sides, and one working electrode of the interdigital array electrode was potentiostated at −0.4 V. Electrolysis of ruthenium hexaamine continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the switches of the switch box 11 were set to the B sides, and the potential of the stripping electrode was swept from −0.4 V to 0.5 V at a scan rate of 20 mV/sec. By the above operations, a peak current of 0.72 μA caused by dissolution of silver was observed at a potential of 0.35 V on a recorder 10. A 1.5-time peak could be observed by activation of the stripping electrode. A reduction waveform of the ruthenium hexaamine cannot be observed by a cyclic voltammogram using one of the working electrodes in the interdigital array electrode due to a background current from dissolved oxygen. The theoretical current value of this type of working electrode can be calculated as 0.68 nA. In this embodiment, a signal could be amplified to about 1,050 times, and a sample having a lower concentration can be measured. Although a similar measurement was performed for an electrolyte which did not contain ruthenium hexaamine, no peak was observed.

As described above, according to this embodiment, a low concentration sample can be measured with an extremely high sensitivity.

(Seventh Embodiment)

As the seventh embodiment, a cell structure of an electrochemical detection apparatus which realize the measurement by only immersed the cell in a sample solution will be described with reference to FIG. 8. A stripping analysis of ruthenium hexaamine as a sample solution will be described.

Figure 8:
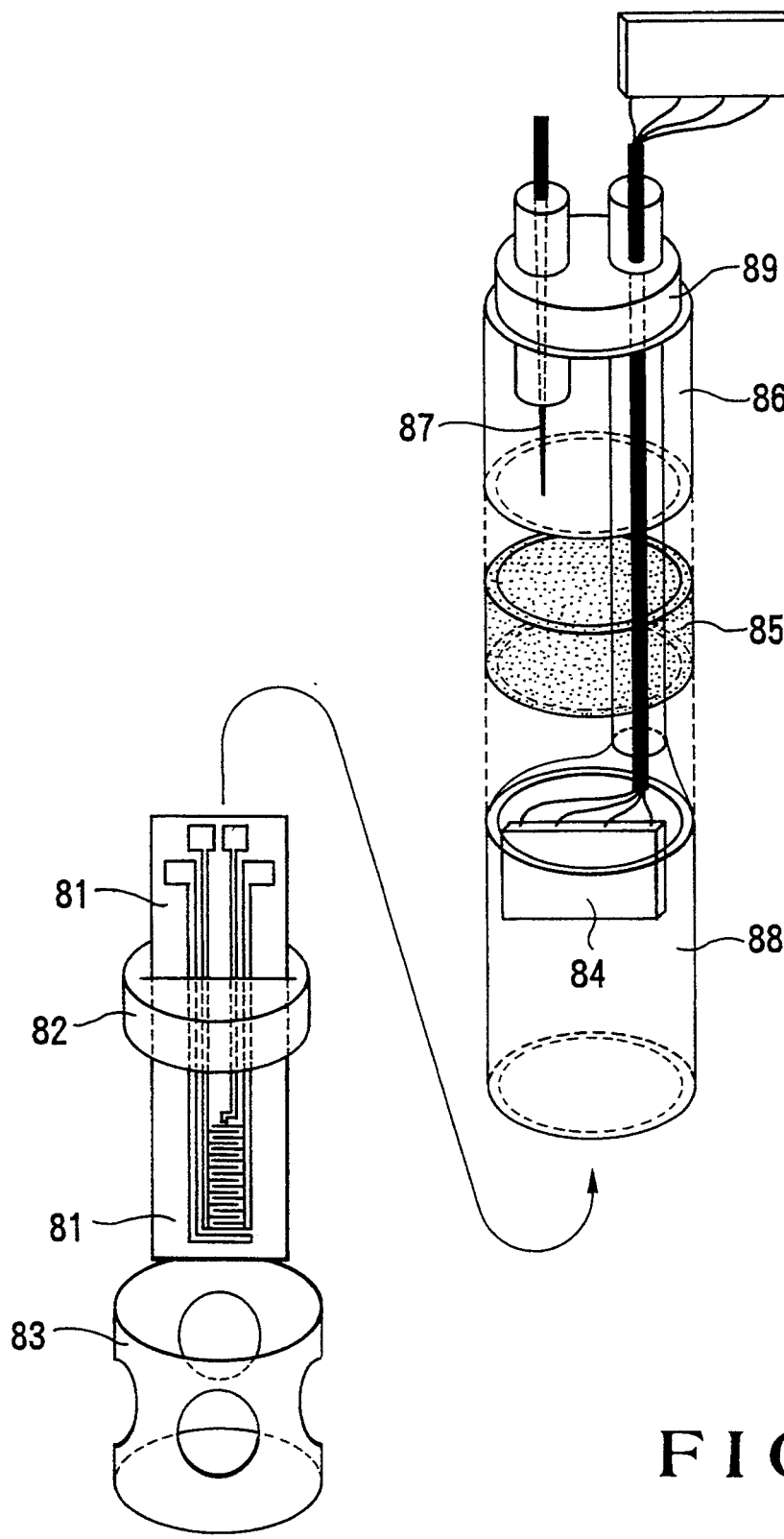
FIG. 8 is a perspective view showing an arrangement of an apparatus according to the seventh embodiment of the present invention.

The cell structure of the electrochemical detection apparatus which realizes measurement by only immersing the cell in a sample solution will be described first, as shown in FIG. 8.

Referring to FIG. 8, a cell 86 corresponds to the auxiliary solution vessel 6 of the basic arrangement of FIG. 1. In the seventh embodiment, the cell is immersed in a sample solution to perform measurement and does not naturally have any part corresponding to the measurement vessel. An interdigital array electrode, a reference electrode, and an auxiliary electrode were formed on a single silicon substrate as an electrode unit 81, applying the same procedures as in the second embodiment.

The electrode unit 81 is inserted into a slit of a cylindrical silicone rubber plug 82 having a diameter of 7 mm, and was sealed with an epoxy resin. An electrode unit protective tube 83 and a lead wire guide cell 88 were connected from below and above the silicone rubber plug 82, respectively, and at the same time the electrode unit 81 is connected to a connector 84. A Vycor glass tube 85 having an outer diameter of 8 mm, a length of 5 mm, and a wall thickness of 1 mm was connected on the lead wire guide cell 88. A stripping cell 86 having an outer diameter of 8 mm was also connected on the Vycor glass tube 85. The lead wire guide cell 88, the Vycor glass tube 85, and the stripping cell 86 were fixed through Teflon heat shrink tubing.

An electrolytic solution containing 0.1 mol/l of potassium nitrate and 1 μmol/l of silver nitrate was filled in the stripping cell 86, and a silicone rubber plug 89 having a hole for guiding a lead wire and a glassy carbon electrode (diameter: 1 mm; length: 2 mm) 87 was mounted in the upper portion of the stripping cell 86, thereby realizing an electrochemical detection apparatus.

An analysis of a sample solution containing a low concentration of ruthenium hexaamine by immersing the electrochemical detection apparatus in the ruthenium hexaamine solution will be described below.

The electrochemical detection apparatus was connected to a potentiostat 9a through a switch box 11 as in the first embodiment. The electrochemical detection apparatus was immersed in a pH 4.2 standard buffer solution (available from Nakarai Chemicals LTD.) containing 1 μmol/l of ruthenium hexaamine until the Vycor glass tube 85 was immersed in the solution.

This electrochemical detection apparatus is used such that a portion thereof below the Vycor glass tube 85 is immersed in a sample. The sample is detected by the lowest part of the electrode unit 81, and stripping is performed in the cell 86. The Vycor glass tube 85 must be immersed in the sample solution so as to cause the Vycor glass tube 85 to work as an ionic conductor.

Operations of the apparatus in this embodiment were performed in two stages as in the previous embodiments.

In pre-electrolysis as the first stage, the switches of the switch box 11 were set on the A sides (FIG. 1), and the potential of one working electrode of the interdigital array electrode was set to be −0.4 V. Electrolysis of ruthenium hexaamine continued for 5 minutes. After the pre-electrolysis, the resultant solution was left for 10 seconds, and the second stage was immediately started.

In the stripping operation as the second stage, the switches of the switch box 11 were set to the B sides, and the potential of the stripping electrode (glassy carbon electrode 87) was swept from −0.4 V to 0.5 V at a scan rate of 20 mV/sec.

By the above operations, a peak current of 3.75 μA caused by oxidation (dissolution) of silver was observed at a potential of 0.35 V on a recorder 10. A reduction waveform of the ruthenium hexaamine cannot be observed by a cyclic voltammogram using one of the working electrodes in the interdigital array electrode due to a background current from dissolved oxygen. The theoretical current value of this type (shape) of working electrode can be calculated as 8 nA. By this embodiment, a signal could be amplified to about 470 times, and it realizes the measurement for a sample having a much lower concentration. Although a similar measurement was performed for an electrolyte without containing ruthenium hexaamine, no peak current was observed.

In repeated measurement by changing the sample solution, it is cumbersome to clean the interior of the cell in the cell structure of the first embodiment. However, this electrochemical detection apparatus is suitable for a simple, quick measurement because the repeated measurement can be made by cleaning only the portion below the Vycor glass tube 84 which contacts the sample solution.

(Eighth Embodiment)

As the eighth embodiment of the present invention, an analysis of a trace amount of vitamin $K_3$ using an electrochemical detection apparatus using a comprising a stepped interdigital array electrode which improves the performance of the interdigital array electrode and a glassy carbon electrode will be described below.

The stepped interdigital array electrode has a structure in which upper and lower electrodes are separated by a thin insulating film. The gap corresponds to the thickness of the insulating layer, so that the gap of the stepped interdigital array electrode can be smaller than that of the interdigital array electrode of the first embodiment. The performance of the electrode can be improved by making the gap smaller. The cell structure is the same as that of the second embodiment.

The fabrication process of the stepped interdigital array electrode will be described with reference to FIGS. 9A to 9G.

As shown in FIG. 9A, a 1-μm thick oxide film 92 was formed on a silicon wafer 91, and chromium and platinum were formed on the oxide film 92 by a sputtering method. Chromium and platinum were sputtered at 50W for 10 seconds and 70W for one minute, respectively, in an argon atmosphere at a pressure of $10^{-2}$ Torr to form a 100-nm thick platinum/chromium thin film.

A photoresist (MP1400-27 available from Shiplay) was coated to a thickness of 1.0 μm on the silicon wafer 91. The silicon wafer 91 coated with this resist was baked on a hotplate at 90° C. for 2 minutes. The resist coated wafer 91 was exposed to UV light through a mask pattern for 15 seconds using a contact mask aligner. The mask pattern was transferred to the photoresist by developing the exposed silicon wafer 91 in a resist developing solution (MF319 available from Shiplay) at 20° C. for 60 seconds. Then, the developed resist was rinsed with water and dried.

The resultant silicon wafer 91 was mounted at a predetermined position in an ion milling apparatus. Platinum/chromium ion milling was performed at an argon gas pressure of $2 \times 10^{-4}$ Torr and an extraction voltage of 550 V for 2 minutes to form the lower electrode. The resist was removed by an ashing apparatus (plasma asher available from Tokyo Ohka) to expose the lower electrode 93 to air, as shown in FIG. 9B.

A 100-nm thick silicon dioxide film 94 was formed on the entire surface of the resultant wafer by using the sputtering method again (FIG. 9C). Chromium and platinum were sequentially sputtered again to form a 100-nm thick platinum/chromium thin film. A photoresist (AZ1400-27 available from Shiplay) was coated to a thickness of 1 μm. An interdigital array pattern was formed by contact photo exposure after alignment of the lower electrode and mask was completed. The resist was developed to obtain the interdigital array pattern, and platinum/chromium ion milling was performed to form an upper electrode. Then, the resist pattern on the upper interdigital array electrode 95 (FIG. 9D) was removed.

A 100-nm thick silicon oxide film 96 was formed on the entire surface of the resultant wafer by using the sputtering method again (FIG. 9E), and a photoresist (AZ1400-27 available from Shiplay) was coated to a thickness of 1 μm. The areas of the photoresist corresponding to the interdigital array electrode (1 μmm×0.25 mm) and the pad areas were exposed to UV light and developed to form a resist pattern 97 (FIG. 9F).

The resultant wafer 91 was placed in a reactive ion etching apparatus, and the silicon dioxide film 96 was etched using the resist pattern as a mask with a $CF_4$ gas at a flow rate of 25 SCCM, a pressure of 0.25 Pa, and a power of 150W for 5 minutes to expose the upper interdigital array electrode 95 and the lower electrode 93 portions between the bands of the upper interdigital array electrode 95 (FIG. 9G). Other electrodes (reference and auxiliary electrodes) can be formed as in formation of the upper interdigital array electrode 95, but are not illustrated in FIGS. 9A to 9G. As a result, the vertically separated interdigital array electrode in which a gap between the upper and lower working electrodes is trace can be obtained.

The reference electrode of this electrode unit was connected to a potentiostat and was immersed in a 70° C. silver plating aqueous solution. Two silver wires for reference and auxiliary electrodes were also immersed in the plating solution. Sliver was plated at a current of 2 μA for 10 seconds to form the reference electrode. The resultant interdigital array electrode was composed of two series comb-like electrodes. The widths of the two comb-like electrodes were both 1.5 μm, and their length was 2 mm. The step and the number of pairs of electrodes were 0.3 μm and 200, respectively. As in the second embodiment, the electrode unit and the glassy carbon electrode (stripping electrode) were connected to a switch box 11 and a potentiostat 9a.

An analysis of a trace amount of vitamin $K_3$ using the apparatus of this embodiment will be described below.

A sample solution for measurement was a pH 4.2 standard buffer solution (available from Nakarai Chemicals LTD.) containing 1 μmol/l of vitamin $K_3$. The auxiliary solution was an electrolytic solution containing 0.1 mol/l of potassium nitrate and 1 μmol/l of silver nitrate.

Operations of the apparatus in this embodiment were performed in two stages as in the previous embodiments.

In pre-electrolysis as the first stage, the switches of the switch box 11 were set on the A sides (FIG. 1), and the potential of one working electrode of the interdigital array electrode of the electrode unit was held at −0.4 V. Electrolysis of vitamin $K_3$ continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the switches of the switch box 11 were set to the B sides, and the potential of the stripping electrode 2 was swept from −0.4 V to 0.5 V at a scan rate of 20 mV/sec.

By the above operations, a peak current of 1.2 μA caused by oxidation (dissolution) of silver was observed at a potential of 0.35 V on a recorder. A reduction waveform of the vitamin $K_3$ cannot be observed by a cyclic voltammogram using one of the working electrodes in the interdigital array electrode due to a background current from dissolved oxygen. The theoretical current value of this type (shape) of working electrode can be calculated as 4 nA. By this embodiment, a signal could be amplified to about 300 times, which realizes the measurement for a sample having a much lower concentration. Although a similar measurement was performed for an electrolyte which did not contain vitamin $K_3$, no peak current was observed.

(Ninth Embodiment)

In the ninth embodiment of the present invention, a pair of band electrodes are used as detection electrodes (working electrodes), a gold amalgam electrode is used as a stripping electrode, and a stripping analysis of a trace amount of ruthenium hexaamine as a sample solution will be described below. The band electrode is a one line electrode, and herein two line electrodes are arranged to form closely spaced electrodes. This electrode structure is very simple and easy to fabricate. Gold was deposited on a silicon wafer having an oxide film thereon, following the same procedures as in the first embodiment. Each electrode had a band width of 2.3 μm and a length of 2 mm, and the electrode gap was 1 μm.

Mercury was adsorbed on the surface of a disk gold electrode having a diameter of 3 mm to obtain a gold amalgam electrode serving as the stripping electrode. The arrangements of a cell and a measurement unit are basically the same as those of FIG. 1.

An analysis of a trace amount of ruthenium hexaamine using the apparatus of this embodiment will be described below.

A sample solution for measurement was a pH 4.2 standard buffer solution containing 1 μmol/l of ruthenium hexaamine. The auxiliary solution was an electrolytic solution containing 0.1 mol/l of potassium nitrate and 1 μmol/l of silver nitrate.

Operations of the apparatus in this embodiment were performed in two stages as in the previous embodiments.

In pre-electrolysis as the first stage, the switches of the switch box 11 were set on the A sides (FIG. 1), and the potential of one of the band electrodes was held at −0.4 V. Electrolysis of ruthenium hexaamine continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the potential of the stripping electrode 2 was swept from −0.4 V to 0.5 V at a scan rate of 50 mV/sec.

By the above operations, a peak current of 0.43 μA caused by oxidation (dissolution) of silver was observed at a potential of 0.35 V on a recorder. A reduction waveform of the ruthenium hexaamine cannot be observed by a cyclic voltammogram using one of the working electrodes in the pair of band electrodes due to a background current from dissolved oxygen. The theoretical current value of this type of working electrode can be calculated as 1.9 nA. By this embodiment, a signal could be amplified to about 230 times, which realizes the measurement for a sample having a much lower concentration can be measured. Although a similar measurement was performed for an electrolyte which did not contain ruthenium hexaamine, no peak current was observed.

As described above, even if the pair of band electrodes having a simple structure are used, a sample having a low concentration can be measured with a high sensitivity.

(Tenth Embodiment)

As the tenth embodiment of the present invention, a stripping analysis of a trace amount of vitamin $K_3$ as a sample solution will be described below. A thin layer cell electrode is used to constitute detection electrodes (working electrodes), and a mercury-modified carbon electrode is used as a stripping electrode.

The thin layer cell electrode had a structure in which two plane electrodes were faced each other. The thin layer cell electrode was fabricated in the following method.

A 1-μm thick resist was coated on an ITO (indium-tin oxide) coated quartz glass substrate. The glass plate is 3 cm long and 1 cm wide. The glass substrate coated with the resist was placed in an oven and baked at 80° C. for 30 minutes.

Contact photo exposure of the substrate was performed by a parallel light mask aligner (PLA-501F available from Canon) using a chromium mask for 20 seconds. The exposed substrate was developed in a resist developing solution (AZ developer available from Shiplay) at 20° C. for 120 seconds to transfer the mask pattern to the resist. The developed substrate was rinsed with water and dried.

ITO film not covered with the resist pattern was etched in a buffered hydrofluoric acid solution. After the etching process, an ITO electrode pattern having a size of 1 $mm^2$ and an ITO lead pattern for electrical connections were formed.

Two glass substrates having an ITO pattern were set to oppose each other such that the ITO electrode surfaces faced each other through a 12.5-μm thick Teflon spacer, thereby forming the thin layer cell electrode.

The stripping electrode was constituted by the mercury-modified carbon electrode obtained by covering with mercury film on a glassy carbon electrode. The arrangements of a cell and a measuring unit are basically the same as those in FIG. 1.

An analysis of a trace amount of vitamin $K_3$ using the apparatus of this embodiment will be described below.

A sample solution for measurement was a pH 4.2 standard buffer solution containing 1 μmol/l of vitamin $K_3$. The auxiliary solution was an electrolytic solution containing 0.1 mol/l of potassium nitrate and 1 μmol/l of salver nitrate.

Operations of the apparatus in this embodiment were performed in two stages as in the previous embodiments.

In pre-electrolysis as the first stage, the potential of one plane electrode of the thin layer electrode cell was held at −0.4 V. Electrolysis of vitamin $K_3$ continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the potential of the stripping electrode 2 was swept from −0.4 V to 0.5 V at a scan rate of 20 mV/sec.

By the above operations, a peak current of 115 nA caused by oxidation (dissolution) of silver was observed at a potential of 0.35 V on a recorder. A reduction waveform of the vitamin $K_3$ cannot be observed by a cyclic voltammogram using one of the plane working electrodes in the thin layer cell electrode due to a background current from dissolved oxygen. The theoretical current value of this type of working electrode can be calculated as 1.1 nA.

In this embodiment, a signal could be amplified to about 105 times, which realizes the measurement for a sample having a much lower concentration. Although a similar measurement was performed for an electrolyte which did not contain vitamin $K_3$, no peak current was observed.

As described above, even if the thin layer cell electrode having a simple structure is used, a sample having a low concentration can be measured with a high sensitivity.

(Eleventh Embodiment)

As the eleventh embodiment of the present invention, 10 interdigital array electrodes are formed on a single substrate and are combined with 10 stripping electrodes. A mixed solution of ruthenium hexaamine and potassium ferrocyanide is used as a sample solution. A simultaneous stripping analysis of 10 pairs of electrodes will be described below.

The purposes of the first to ninth embodiments are to detect a trace amount of analyte in the sample solution. However, the purpose of the eleventh embodiment is to measure the redox potential significant which is important to distinguish the analyte in a sample solution even if the analyte concentration is low.

The structure of this embodiment is basically constituted by arranging 10 pairs of the detection electrode units (first embodiment) and 10 stripping electrodes 2. The detection electrode unit and the stepping electrode are basically the same as in the first embodiment. A 10-channel potentiostat (HECS966 available from Huso), a 10-channel recorder (WR8000 available from Graphtec), and a 10-channel switch box were used for measurement. The interdigital array electrode of the detection electrode unit is composed of two series comb-like electrodes (1a and 1b) used in this embodiment. The widths of the two comb-like electrodes were both 2 μm, and their length was 2 min. The gap and the number of pairs of electrodes were 2 μm and 75, respectively. The 10 interdigital array electrodes were fabricated on the same substrate.

The 10 stripping electrodes were constituted by 10 glassy carbon electrodes whose diameter was 1 mm.

An analysis of a trace amount of ruthenium hexaamine and potassium ferrocyanide mixed solution using the apparatus having the arrangement described above will be described below.

A sample solution was a pH 4.2 standard buffer solution containing 1 μmol/l of ruthenium hexaamine and 1 μmol/l of potassium ferrocyanide. The auxiliary solution was an electrolytic solution containing 0.1 mol/l of potassium nitrate and 1 μmol/l of silver nitrate.

Operations of the apparatus in this embodiment were performed in two stages as in the previous embodiments.

In pre-electrolysis as the first stage, the ten working electrodes in the ten interdigital array electrodes (which means one of the electrodes in each interdigital array electrode) were held at the different potentials which were potentiostated at 0.1 V intervals from −0.4 to 0.5 V. Electrolysis of the sample solution for measurement continued for 10 minutes. During this period, the auxiliary solution was kept stirring. After the pre-electrolysis, stirring of the auxiliary solution was immediately stopped. The resultant solution was left for 10 seconds, until the solution became still. The second stage was then immediately started.

In the stripping operation as the second stage, the potentials of all the 10 stripping electrodes 2 were simultaneously swept from −0.4 V to 0.5 V at a scan rate of 20 mV/sec.

By the above operations, peak waveforms having different magnitudes according to the held potentials in the pre-electrolysis were observed at a potential of 0.35 V on a recorder. The magnitudes of the peak currents were plotted as a function of the pre-electrolysis potentials. A waveform having a first-staircase wave rising from −0.3 V and started to saturate at −0.1 V and a second-staircase wave rising from 0.1 V and started to saturate at 0.3 V were obtained. When measurement was made for a sample solution which contained only 1 μmol/l of potassium ferrocyanide, the first-staircase wave disappeared, and only the second-staircase wave was obtained.

The above results clearly indicate that the redox reaction of ruthenium hexaamine corresponded to the first-staircase wave, and its redox potential was about −0.2 V. Potassium ferrocyanide corresponded to the second-staircase wave, and its redox potential was about 0.2 V. The magnitudes of first- and second-staircase waves are larger than those obtained in a conventional cyclic voltammogram due to the pre-electrolysis stage (first step) in the stripping measurement. Therefore, this measurement is suitable for a sample having a low concentration.

By this embodiment, as described above, the redox potential of a solution having a low concentration can be realized.

(Twelfth Embodiment)

As the twelfth embodiment of the present invention, a cathodic stripping analysis of a trace amount of ag-ferrocene as a sample solution for measurement will be described below.

The analytes of the first to eleventh embodiments existing in the solutions are an oxidized form. On the other hand, since aq-ferrocene (ferrocenylmethyltrimethylammonium bromide) exits in the reduced form, the measurement of aq-ferrocene is different from that of the oxidized form. The arrangements of detection electrodes, a cell, and a measuring unit are the same as those of the first embodiment. A stripping electrode 2 was constituted by a silver disk electrode whose diameter was 3 mm.

An analysis of a trace amount of the aq-ferrocene using the apparatus having the above arrangement will be described below.

A sample solution for measurement was a pH 7 phosphate buffer solution containing 1 μmol/l of aq-ferrocene. The auxiliary solution was an electrolytic solution containing 0.1 mol/l of potassium nitrate and 1 μmol/l of potassium iodide.

Operations of the apparatus in this embodiment were performed in two stages as in the previous embodiments.

In pre-electrolysis as the first stage, the potential of one working electrode In the interdigital array electrode was held at 0.55 V. Electrolysis of aq-ferrocene continued for 10 minutes. During this period, the auxiliary solution was kept stirring. After the pre-electrolysis, stirring of the auxiliary solution was stopped. The resultant solution was left for 10 seconds, until the solution became still. The second stage was then started.

In the stripping operation as the second stage, potential application to the detection electrode (working electrode) was stopped, and the potential of the stripping electrode 2 was swept from 0.2 V to −0.4 V at a scan rate of 20 mV/sec.

By the above operations, a peak current of 8 μA caused by the reduction (dissolution) of iodine was observed at a potential of −0.15 V on a recorder. A peak current of 8 nA was obtained by a cyclic voltammogram of aq-ferrocene using one working electrode of the interdigital array electrode. By this embodiment, a signal could be amplified to about 1,000 times, which realizes the measurement for a sample having a lower concentration. Although a similar measurement was performed for an electrolyte which did not contain aq-ferrocene, no peak current was observed.

As described above, the low concentration of analyte dissolved in the sample solution as a reduced form can be detected with a high sensitivity.

(Thirteenth Embodiment)

As the thirteenth embodiment of the present invention, a cathodic stripping analysis of a trace amount of dihydroxybenzylamine in a sample solution for measurement will be described below.

Dihydroxybenzylamine exits as a reduced form in a sample solution. The arrangements of detection electrodes, a cell, and a measuring unit are the same as those of the first embodiment. A stripping electrode was constituted by a silver disk electrode whose diameter was 3 mm.

An analysis of a trace amount of dihydroxybenzylamine using the apparatus having the arrangement above will be described below.

A sample solution for measurement was a pH 7 phosphate buffer solution containing 1 μmol/l of dihydroxybenzylamine. The auxiliary solution was an electrolytic solution containing 0.1 mol/l of potassium nitrate and 1 μmol/l of potassium iodide.

Operations in this embodiment were performed in two stages as in the previous embodiments.

In pre-electrolysis as the first stage, the potential of one working electrode in the interdigital array electrode of the detection electrode unit was held at 0.45 V. Electrolysis of dihydroxybenzylamine continued for 10 minutes. During this period, the auxiliary solution was kept stirring. After the pre-electrolysis, stirring of the auxiliary solution was stopped. The resultant solution was left for 10 seconds, until the solution became still. The second stage was then started.

In the stripping operation as the second stage, potential application to the working electrode of the interdigital array electrode of the detection electrode unit was stopped, and the potential of the stripping electrode 2 was swept from 0.2 V to −0.4 V at a scan rate of 20 mV/sec.

By the above operations, a peak current of 4 μA caused by reduction (dissolution) of iodine was observed at a potential of −0.15 V on a recorder. A peak current of 17 nA was observed by a cyclic voltammogram of dihydroxybenzylamine using one working electrode of the interdigital array electrode. By this embodiment, a signal could be amplified to about 250 times, which realizes the measurement for a sample having a lower concentration. Although a similar measurement was performed for an electrolyte which did not contain dihydroxybenzylamine, no peak current was observed.

In this embodiment, the low concentration of analyte in the solution can be detected with a high sensitivity.

As described in these thirteen embodiments, the electrochemical detection apparatus of the present invention utilizes the potential difference induced by a concentration gradient of an analyte formed by the pre-electrolysis of the analyte on the closely spaced microelectrode pair.

By this potential difference, the charge generated by the self-induced redox cycling of the analyte is converted to the accumulation of the materials such as metal ions or halide on the stripping electrode.

The stripping current can be obtained by electrochemically oxidizing/reducing the accumulated materials at once.

The signal is greatly amplified by measuring the converted material which is accumulated in the pre-electrolysis stage.

In the conventional stripping analysis, the application field is limited because only the metal ions or halide can be detected.

However, the application field could be enhanced by the present invention, because various types of redox species can be detected by using the stripping method of the present invention.

Similar to the conventional stripping analysis, the magnitude of signal (gain) in the stripping analysis of the present invention can be controlled by changing the pre-electrolysis time and the scan rate of the stripping.

Since the electrochemical cells can be fabricated using lithographic techniques, inexpensive cells integrating working, reference, and auxiliary electrodes with any required shape and size can be realized with excellent reproducibility.

The distance between the electrodes can also be controlled using the lithographic techniques.

The apparatus of the present invention will have a wide application field as an analysis equipment for trace amounts of materials because the total system is very simple.

What is claimed is:

1. An electrochemical detection method using an apparatus including
   a first vessel and a second vessel,
   a reference electrolytic solution filled in said second vessel,
   first and second closely spaced working electrodes immersed in a sample solution for measurement filled in said first vessel,
   a stripping electrode immersed in the reference electrolytic solution, and
   an ionic conductor, arranged between said first vessel and said second vessel, for electrically connecting the sample solution for measurement and the reference electrolytic solution, wherein
   the reference electrolytic solution contains an electrolyte which can be deposited and dissolved by an electrochemical reaction by applying a potential to said stripping electrode,
   in a first stage, a pre-electrolysis potential is applied to said first working electrode with said stripping electrode being connected to said second working electrode to deposit the electrolyte in the reference electrolytic solution on said stripping electrode, and
   in a second stage, after said second working electrode is disconnected from said stripping electrode, the potential of said stripping electrode is swept to measure a current generated when the electrolyte deposited on said stripping electrode in the first stage is dissolved from said stripping electrode, and the concentration of an analyte in the sample solution for measurement is determined from the measured stripping current.

2. A method according to claim 1, further including the utilization of a reference electrode and an auxiliary electrode in the sample solution filled in said first vessel.

3. A method according to claim 1, wherein said ionic conductor comprises a salt bridge.

4. A method according to claim 3, further including the utilization of reference and auxiliary electrodes in an electrolytic solution in said salt bridge.

5. A method according to claim 1, further including the utilization of reference and auxiliary electrodes, which are arranged in said first vessel or said second vessel or said salt bridge arranged between said first and second vessels.

6. An electrochemical detection apparatus including
   a first vessel and a second vessel,
   a reference electrolytic solution filled in said second vessel,
   first and second closely spaced working electrodes immersed in a sample solution for measurement filled in said first vessel,
   a stripping electrode immersed in the reference electrolytic solution, and
   an ionic conductor, arranged between said first vessel and said second vessel, for electrically connecting the sample solution for measurement and the reference electrolytic solution, wherein
   the reference electrolytic solution contains an electrolyte which can be deposited and dissolved by an electrochemical reaction by applying a potential to said stripping electrode, and
   said apparatus comprises
   means for, in a first stage, applying a pre-electrolysis potential to said first working electrode with said stripping electrode being connected to said second working electrode to deposit the electrolyte in the reference electrolytic solution on said stripping electrode,
   means for, in a second stage, disconnecting said second working electrode from said stripping electrode,
   means for, in the second stage, sweeping a potential of said stripping electrode after said second working electrode is disconnected from said stripping electrode, and means for, in the second stage, measuring a current generated when the electrolyte deposited on said stripping electrode in the first stage is dissolved from said stripping electrode.

7. An apparatus according to claim 6, further comprising reference and auxiliary electrodes in the sample solution filled in said first vessel.

8. An apparatus according to claim 6, wherein said ionic conductor comprises a salt bridge.

9. An apparatus according to claim 8, further comprising reference and auxiliary electrodes in an electrolytic solution in said salt bridge.

10. An apparatus according to claim 6, comprising at least two sets of first, second, and stripping electrodes.

11. An apparatus according to claim 6, further comprising reference and auxiliary electrodes, which are arranged in said first vessel or said second vessel or said salt bridge arranged between said first and second vessels.

12. An apparatus according to claim 6, wherein
said first and second vessels comprise
an insulating substrate and
a cell frame fixed on said substrate so as to have a measurement region hole and a reference region hole, and
said ionic conductor is arranged between said measurement and reference region holes of said cell.

13. An apparatus according to claim 12, wherein each of said electrodes is formed on said substrate.

* * * * *